(12) United States Patent
Komatsu et al.

(10) Patent No.: US 6,241,947 B1
(45) Date of Patent: Jun. 5, 2001

(54) CHEMICAL ANALYSIS SYSTEM AND BLOOD FILTERING UNIT

(75) Inventors: Akihiro Komatsu; Kenji Arai, both of Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/236,591

(22) Filed: Jan. 26, 1999

(30) Foreign Application Priority Data

Jan. 27, 1998 (JP) .................................................. 10-014466
Jan. 27, 1998 (JP) .................................................. 10-014468

(51) Int. Cl.$^7$ .................................................. G01N 33/00
(52) U.S. Cl. ........................... 422/67; 422/68.1; 422/99; 422/100; 422/101
(58) Field of Search .................................. 422/61, 67, 63, 422/62, 99, 101, 68.1, 100; 604/4–7; 210/97, 98, 100, 143, 321.6, 371.72, 406

(56) References Cited

U.S. PATENT DOCUMENTS

| 4,152,390 | * | 5/1979 | Nosco et al. ............................. 422/63 |
| 4,257,862 | | 3/1981 | Schnipelsky et al. ........... 204/195 R |
| 4,296,069 | | 10/1981 | Smith et al. ............................. 422/64 |
| 4,854,322 | * | 8/1989 | Ash et al. ............................. 128/635 |
| 4,994,188 | * | 2/1991 | Prince ................................... 210/636 |
| 5,018,527 | * | 5/1991 | Pfab et al. ............................. 128/635 |
| 5,171,532 | * | 12/1992 | Columbus et al. ..................... 422/72 |
| 5,486,477 | * | 1/1996 | Carver, Jr. ............................. 436/17 |
| 5,738,644 | * | 4/1998 | Holmes et al. ............................. 604/4 |
| 5,876,611 | * | 3/1999 | Shettigar ............................. 210/739 |

FOREIGN PATENT DOCUMENTS

| 44-14673 | 6/1969 | (JP) | .................... 113/21 A |
| 58-4981 | 1/1983 | (JP) | .............. G01N/27/30 |
| 58-156848 | 9/1983 | (JP) | .............. G01N/27/30 |
| 58-211648 | 12/1983 | (JP) | .............. G01N/27/46 |
| 61-26864 | 2/1986 | (JP) | .............. G01N/35/04 |
| 2-208565 | 8/1990 | (JP) | .............. G01N/33/48 |
| 4-208856 | 7/1992 | (JP) | .............. G01N/33/48 |
| 5-52463 | 8/1993 | (JP) | .............. G01N/33/48 |
| 6-66818 | 3/1994 | (JP) | .............. G01N/35/04 |
| 6-82113 | 10/1994 | (JP) | .............. G01N/27/28 |
| 9-196911 | 7/1997 | (JP) | .............. G01N/33/48 |
| 9-276631 | 10/1997 | (JP) | .............. B01D/39/18 |

* cited by examiner

Primary Examiner—T. Tung
Assistant Examiner—Dwayne K Handy
(74) Attorney, Agent, or Firm—Sughrue, Mion, Zinn, Macpeak & Seas, PLLC

(57) ABSTRACT

A chemical analysis system for analyzing a sample liquid spotted on a chemical analysis element includes a blood filtering unit, a spotting mechanism which spots the filtrate of the blood filtering unit onto the chemical analysis element as the sample liquid, and an analyzer which analyzes the filtrate on the chemical analysis element. The blood filtering unit includes a filter which filters whole blood to obtain filtrate, a holder which holds the filter and has a blood inlet and a filtrate outlet, a suction system which is removably connected to the filtrate outlet side of the holder and applies a negative pressure to the holder from the filtrate outlet side, and a filtrate receiving container disposed on the filtrate outlet side of the holder to receive the filtrate.

9 Claims, 17 Drawing Sheets

FIG.13
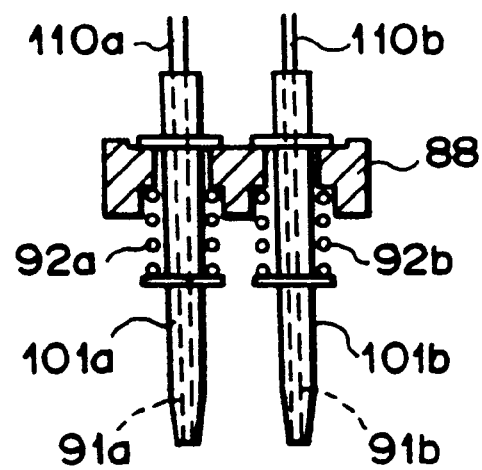
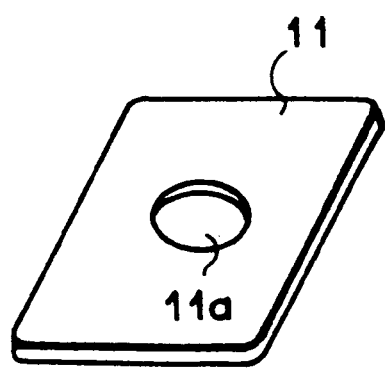
FIG.14A
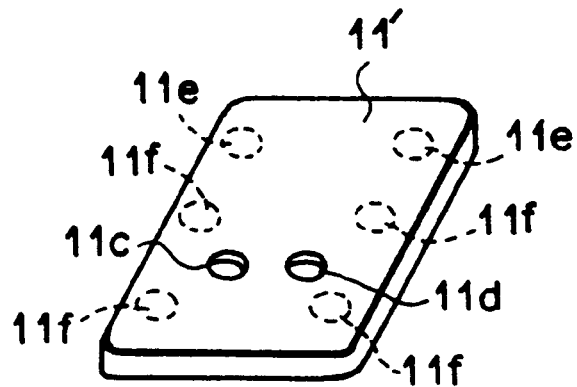
FIG.14B

CHEMICAL ANALYSIS SYSTEM AND BLOOD FILTERING UNIT

BACKGROUND OF THE INVENTION

1. Field of the Invention

This invention relates to a chemical analysis system for determining a concentration of a predetermined chemical component in a sample liquid such as blood, urine or the like spotted on a chemical analysis element and for determining an activity of a specific ion in a sample liquid such as blood, urine or the like spotted on a chemical analysis element and to a blood filtering unit for separating blood plasma, serum or the like from whole blood.

2. Description of the Related Art

There has been put into practice a dry ("dry-to-the-touch") chemical analysis element with which a specific chemical component or a solid component contained in a sample liquid can be quantitatively analyzed by only spotting a droplet of the sample liquid onto the element.

When quantitatively analyzing the chemical components or the like contained in a sample liquid using such a dry chemical analysis element, a droplet of the sample liquid is spotted onto the element and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the element is projected onto the element and the optical density of the element is measured. Then the concentration of the component to be analyzed is determined on the basis of the optical density using a standard curve which represents the relation between the concentration of the biochemical component and the optical density.

In the chemical analysis system, the chemical analysis elements are transferred to the incubator one by one in sequence and taken out from the incubator to be discarded after measurement of the concentration. For example, as disclosed in Japanese Unexamined Patent Publication No. 61(1986)-26864, U.S. Pat. No. 4,296,069, the chemical analysis elements are carried in a disc-like incubator from the outer side of the incubator and taken out from the outer side of the same by ejecting the chemical analysis element from the inner side of the same or drawing out the chemical analysis element from the outer side of the incubator.

Further there has been known a chemical analysis system in which the incubator is rotatable about its axis and has a plurality of chemical analysis element receiving portions arranged in a circle about the axis of rotation of the incubator and each chemical analysis element is inserted into one of the receiving portions by a conveyor means which conveys the chemical analysis element linearly toward the axis of rotation of the incubator and is pushed further toward the axis of rotation of the incubator by the conveyor means, after measurement of the concentration, into a discarding hole which opens at the center of the incubator. (See Japanese Unexamined Patent Publication No. 6(1994)-66818.)

Further there has been known an ionic activity measuring system for measuring an activity of a specific ion contained in a sample liquid as disclosed, for instance, in U.S. Pat. No. 4,257,862, Japanese Patent Publication No. 58(1983)-4981, Japanese Unexamined Patent Publication Nos. 58(1983)-156848 and 58(1983)-211648 and Japanese Patent Publication No. 6(1994)-82113. A chemical analysis element used in such an ionic activity measuring system comprises a pair of ion selective electrodes and a porous bridge which connects the ion selective electrodes. When a reference liquid containing therein the specific ion whose ionic activity is known is spotted onto one of the ion selective electrodes and a sample liquid containing therein the specific ion whose ionic activity is not known is spotted onto the other ion selective electrode, the reference liquid and the sample liquid come to electrically contact with each other through the porous bridge and a potential difference is produced between the ion selective electrodes according to the difference in the ionic activity between the specific ions contained in the sample liquid and the reference liquid. The ionic activity of the specific ion in the sample liquid can be determined according to the potential difference on the basis of a standard curve which has been obtained in advance according to Nernst equation.

It is preferred that the ionic activity measuring system for measuring the ionic activity of a specific ion in a sample liquid using such a chemical analysis element be in the form of an analyzer which is provided with both function to spotting the sample liquid and the reference liquid onto the ion selective electrodes and function to measure the potential difference. In such an analyzer, the chemical analysis element spotted with the sample liquid and the reference liquid is transferred to a potential difference measuring section, where potential measurement probes are brought into contact with the ion selective electrodes to measure the potential difference between the electrodes.

Further when the biochemical component contained in blood is analyzed or the activity of a specific ion in blood is measured, generally blood plasma or serum is separated from the whole blood and the blood plasma or the serum separated from the whole blood is used as the sample liquid. Conventionally the blood plasma and the serum are separated from the whole blood by centrifuging. However centrifuging takes a long time and a lot of labor. Accordingly it is difficult to deal with an emergency. Further, when a plurality of samples are to be processed in a short time and/or the samples are to be processed on the spot, use of a motorized centrifugal separator is inconvenient. Accordingly, there have been a demand for a method of separating the plasma or serum by filtration.

There have proposed various methods of separating blood plasma in which whole blood is poured into a column filled with glass fiber filter paper and various microporous membranes such as of cellulose acetate from one end of the column and blood plasma is extracted from the other end of the column while increasing or reducing the pressure in the column. See, for instance, Japanese Patent Publication Nos. 44(1969)-14673 and 5(1993)-52463 and Japanese Unexamined Patent Publication Nos. 2(1990)-208565 and 4(1992)-208856.

However, at present, there has not been developed a method which can separate blood plasma or serum from whole blood in an amount necessary for measurement of the concentration of a specific component or measurement of the activity of a specific ion.

We have developed a blood filtering system which can efficiently separate blood plasma and/or serum from a fine amount of blood. In this blood filtering system, a combination of glass fiber filter paper and microporous membrane is employed as the filer medium and a seal member is provided on the plasma outlet side of the filter medium to reduce the opening area of the filter medium. See Japanese Patent Application No. 8(1996)-7692. Further in the blood filtering system disclosed in Japanese Patent Application No. 8(1996)-91621, a plasma receiving container is provided on the plasma outlet side of the filter medium.

However these blood filtering systems are disadvantageous in that since the whole blood is filtered by simply applying suction force to the whole blood, filtration takes a long time when the suction force is too weak while the components of the blood can be destroyed when the suction force is too strong.

SUMMARY OF THE INVENTION

In view of the foregoing observations and description, the primary object of the present invention is to provide a chemical analysis system in which blood plasma or serum can be quickly separated from the whole blood and the blood can be analyzed in a short time.

Another object of the present invention is to provide a blood filtering system in which blood plasma or serum can be filtered from the whole blood in a short time without fear that the components of the blood are destroyed.

In accordance with a first aspect of the present invention, there is provided a chemical analysis system for analyzing a sample liquid spotted on a chemical analysis element comprising a blood filtering unit comprising a filter means which filters whole blood to obtain filtrate, a holder which holds the filter and has a blood inlet and a filtrate outlet, a suction means which is removably mounted on the filtrate outlet side of the holder and applies a negative pressure to the holder from the filtrate outlet side, and a filtrate receiving container disposed on the filtrate outlet side of the holder to receive the filtrate, a spotting means which spots the filtrate onto the chemical analysis element as the sample liquid, and an analyzing means which analyzes the filtrate on the chemical analysis element.

In one embodiment, the analyzing means comprises both a concentration measuring means which is provided to measure the concentration of the specific component contained in the sample liquid by measuring the optical density of the color formed by the coloring reaction of the sample liquid and a reagent on the chemical analysis element and an ionic activity measuring means which is provided to measure the ionic activity of the specific ion contained in the sample liquid.

It is preferred that there is further provided a diluting unit which includes a sample liquid container and dilutes the sample liquid in the container with diluent.

In the chemical analysis system of the present invention, since the blood filtering unit is provided, blood can be quickly analyzed by simply supplying whole blood taken from a case. That is, when the whole blood taken from the case, the blood filtering unit filters the whole blood to obtain blood plasma or serum, and the spotting means spots the blood plasma or the serum as the sample liquid. The analyzing means analyzes the plasma or the serum. Since the blood filtering unit obtains the plasma or the serum by filtration under reduced pressure, the plasma or the serum can be obtained in a shorter time as compared with when the plasma or the serum is obtained centrifugal separation, and it is possible to deal with an emergency.

When a diluting unit which dilutes the sample liquid is provided, a sample liquid which is desired to be analyzed in a diluted state can be quickly analyzed.

In accordance with a second aspect of the present invention, there is provided a blood filtering unit comprising a filter means which filters whole blood to obtain filtrate, a holder which holds the filter and has a blood inlet and a filtrate outlet, a suction means which is removably mounted on the filtrate outlet side of the holder and applies a negative pressure to the holder from the filtrate outlet side, a pressure detecting means which detects the suction pressure of the suction means, and a control means which controls the suction speed of the suction means on the basis of the suction pressure detected by the pressure detecting means so that the suction pressure is held at a predetermined value.

It is preferred that there is provided a judging means which judges the suction state of the suction means on the basis of comparison of the suction pressure detected by the pressure detecting means and the predetermined value and/or comparison of the suction speed of the suction means and a predetermined sucking speed.

Further it is preferred that there is provided an error signal generating means which generates an error signal when the suction pressure detected by the pressure detecting means becomes lower than the predetermined value and/or when the suction speed of the suction means exceeds the predetermined suction speed.

Further it is preferred that there is provided a stopping means which stops the suction means when the error signal is generated or a pressure relief means which releases the negative pressure to the atmosphere when the error signal is generated.

In the blood filtering unit of this invention, since the suction speed of the suction means is controlled on the basis of the suction pressure detected by the pressure detecting means so that the suction pressure is held at a predetermined value, the blood can be filtered at an optimal suction pressure.

When the judging means which judges the sucking state of the suction means is provided, abnormality in the suction state of the suction means, e.g., when the negative pressure leaks or when there is no whole blood to be filtered, can be easily detected. It is possible to give the alarm or immediately stop the blood filtering unit when the judging means detects abnormality in the suction state of the suction means.

BRIEF DESCRIPTION OF THE DRAWINGS

FIG. 13 is a fragmentary enlarged view as seen in the direction of arrow A in FIG. 12, FIG. 14A is a perspective view of the chemical analysis element for measuring the optical density, FIG. 14B is a perspective view of the chemical analysis element for measuring the ionic activity.

DESCRIPTION OF THE PREFERRED EMBODIMENTS

Figure 1:
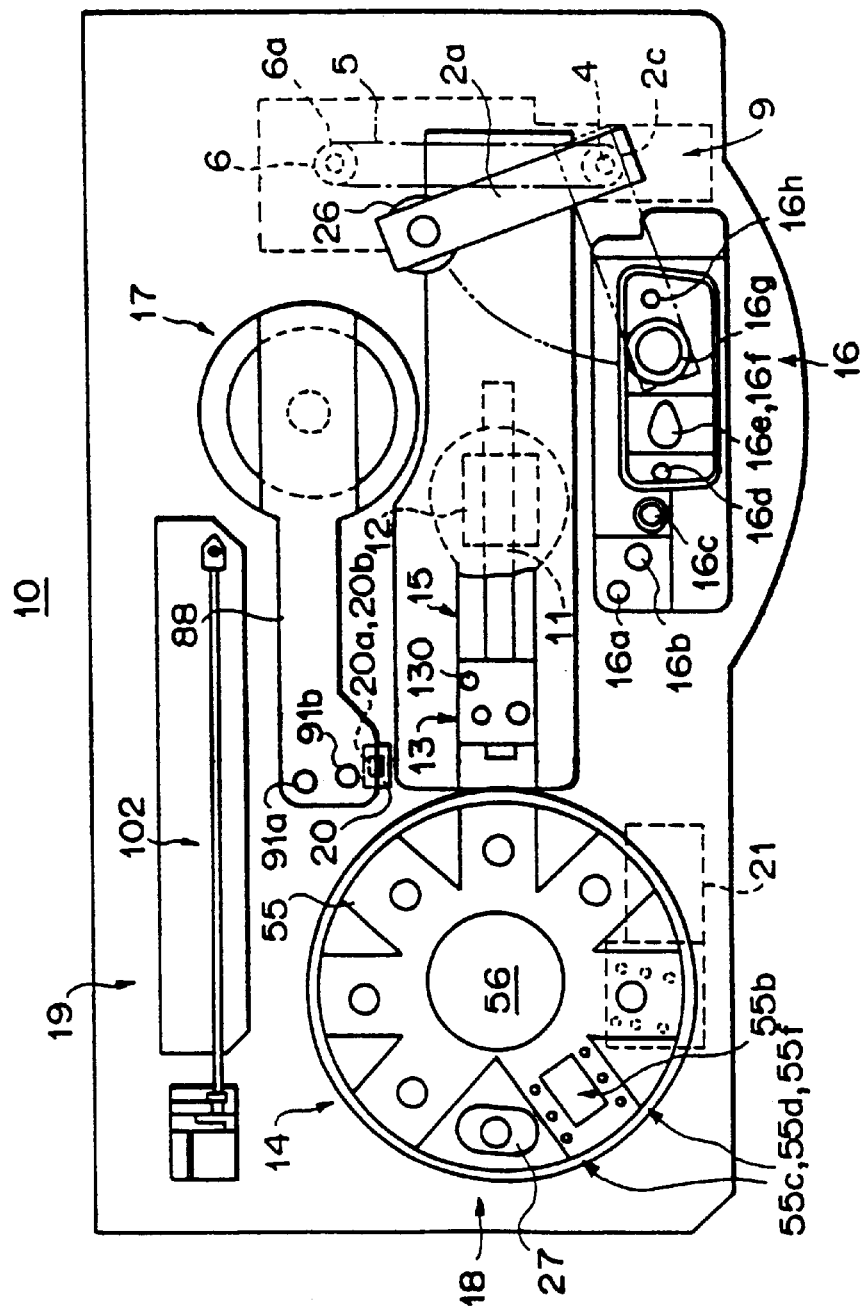
FIG. 1 is a schematic plan view of an important part of the chemical analysis system in accordance with an embodiment of the present invention.

In FIG. 1, a chemical analysis system 10 in accordance with an embodiment of the present invention comprises a blood plasma filtering unit 9 which separates blood plasma from blood, a chemical analysis element supply section 12 in which a plurality of virgin chemical analysis elements 11 for measuring the concentration of a specific component in blood plasma and/or virgin chemical analysis elements 11' for measuring the ionic activity of a specific ion in blood plasma (both the chemical analysis elements 11 and 11' will be sometimes represented by 11, hereinbelow) are contained, a spotting station 13 at which a sample liquid (blood plasma in this particular embodiment but may be whole blood, blood serum, urine or the like) and/or a reference liquid or a diluent liquid in a sample holding portion 16 is spotted onto the chemical analysis element 11 as will be described in detail later, and an incubator 14 which receives therein the chemical analysis elements 11 and holds the chemical analysis elements 11 at a constant temperature for a predetermined time. A conveyor means 15 conveys the chemical analysis elements 11 one by one from the element supply section 12 to the spotting station 13. At the spotting station 13, a spotting means 17 spots a predetermined amount of the sample liquid (blood plasma) and/or the reference liquid onto the chemical analysis element 11 as will be described in detail later. Then the chemical analysis element 11 spotted with the sample liquid is inserted into a chemical analysis element receiving portion 55 in the incubator 14 by the conveyor means 15. After the chemical analysis element 11 is incubated for a predetermined time, the optical density of the chemical analysis element 11 is measured by a light measuring head 27 of a measuring means 18 or the ionic activity of the sample liquid spotted onto the chemical analysis element 11' is measured by an analyzer 21. After the measurement, the chemical analysis element 11 is dropped into a discarding hole 56 at the center of the incubator 14 by the conveyor means 15.

FIG. 14A shows the chemical analysis element 11 for measuring the concentration of a specific chemical component in the sample liquid. As shown in FIG. 14A, the chemical analysis element 11 comprises a square mount in which a reagent layer is provided and the reagent layer is exposed through a spotting hole 11a. Blood plasma is spotted onto the reagent layer through the spotting hole 11a. FIG. 14B shows the chemical analysis elements 11' for measuring the ionic activity of a specific ion in the sample liquid. As shown in FIG. 14B, the chemical analysis element 11' is substantially the same in shape as the chemical analysis element 11 for measuring the concentration of a specific chemical component in the sample liquid and is provided with a pair of spotting holes 11c and 11d. As will be described later, blood plasma is spotted onto the spotting hole 11c and a reference liquid is spotted onto the spotting hole 11d. Further the chemical analysis element 11' is provided with three pairs of ion selective electrodes 11e, 11f and 11g, each pair of ion selective electrodes being brought into electrical contact with the electrodes of the analyzer 21. The pairs of the ion selective electrodes 11e, 11f and 11g are provided with ion selective layers which are selective to $Cl^-$, $K^+$ and $Na^+$, respectively. A bar code for identifying terms of examination and the like is recorded on the back surface of the chemical analysis element 11(11').

Figure 2:
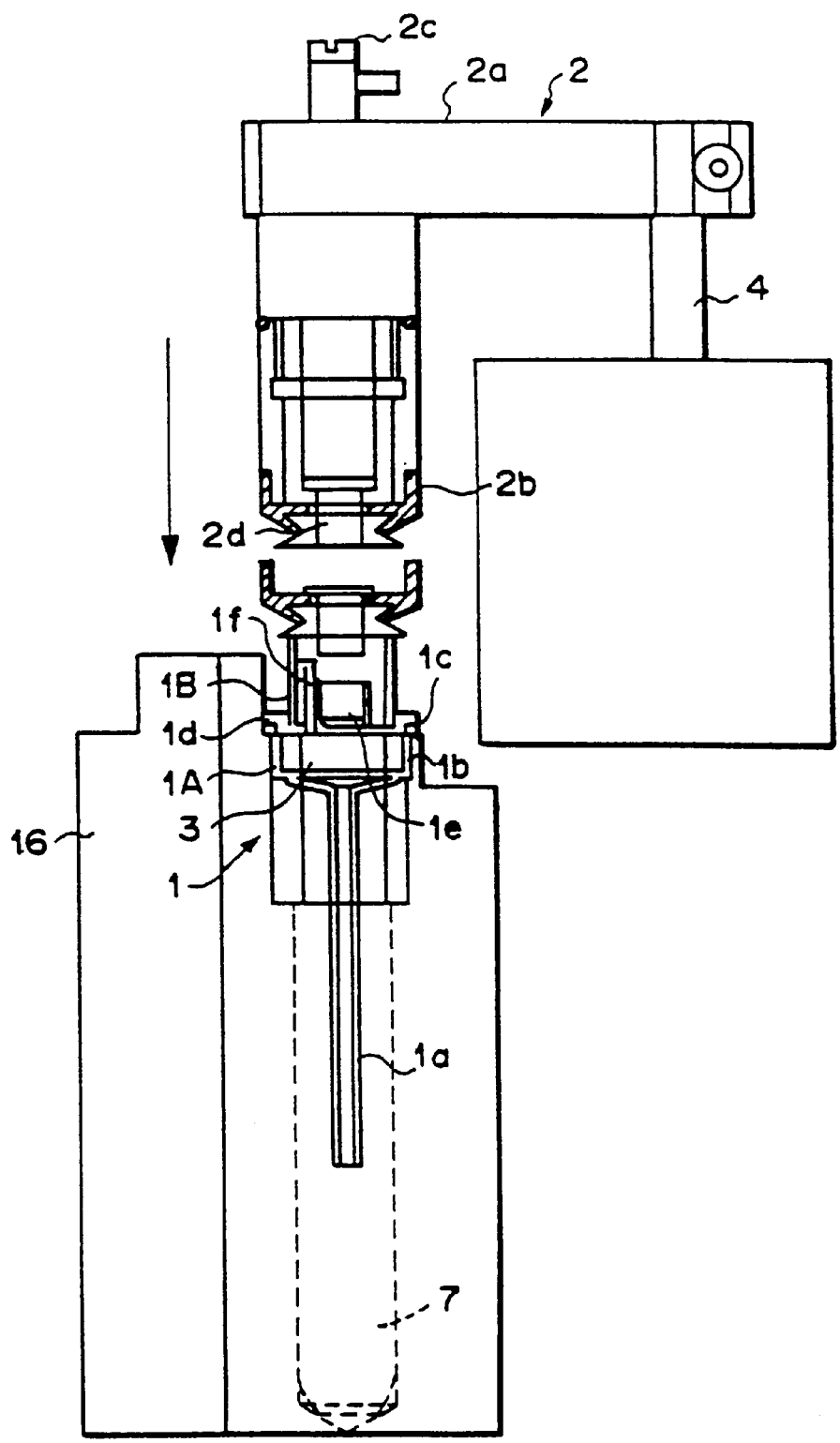
FIG. 2 is a schematic front view showing the blood filtering unit.
Figure 3:
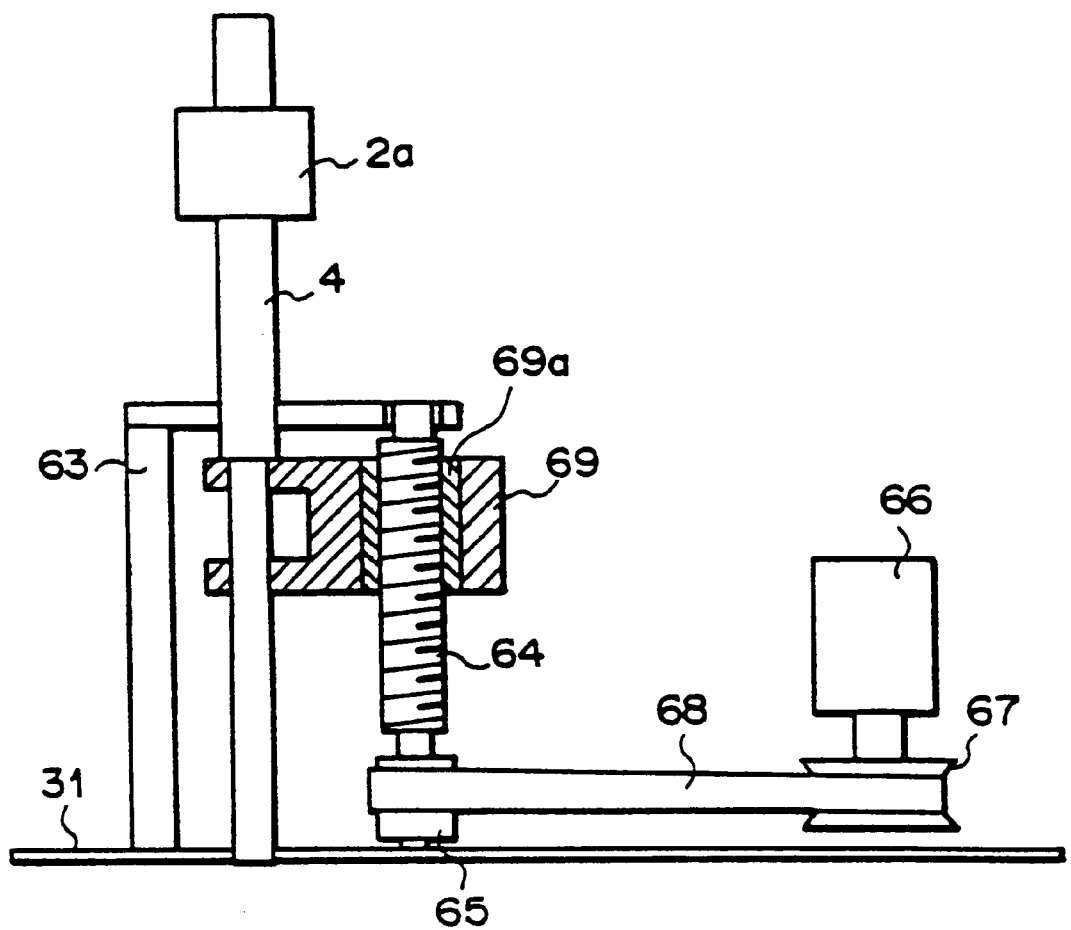
FIG. 3 is a schematic side view showing the blood filtering unit.

As shown in FIGS. 2 and 3, the blood plasma filtering unit 9 comprises a holder 1 which is mounted on the open end of a blood-gathering tube 7 placed in the sample holding portion 16 and a sucking means 2 which is connected to the holder 1 and supplies negative pressure for separating blood plasma from blood to the tube 7. The holder 1 comprises a body portion 1A and a lid member 1B which are formed of plastic. The body portion 1A comprises a plug portion 1a which is inserted into the tube 7, a filter holding portion 1b into which a filter 3 of a glass fiber or the like is inserted, and a flange portion 1c. The lid member 1B comprises a flange portion 1d, a cup 1e for holding blood plasma filtered by the filter 3 and a supply nozzle 1f which supplies blood plasma from the filter 3 to the cup 1e. The lid member 1B is bonded to the body portion 1A by bonding the flange portions 1c and 1d together, for instance, by ultrasonic welding.

The sucking means 2 comprises an arm 2a mounted on a shaft member 4 which is supported for rotation on a base 31. A suction pad portion 2b which is brought into abutment against the lid member 1B of the holder 1 is provided on the lower end of the arm 2a. The suction pad portion 2b is connected to a negative pressure supply portion 2c which is connected to a pump (to be described later) and supplies a negative pressure to the suction pad portion 2b. The negative pressure supply portion 2c is provided with a pressure relief valve (not shown) for cutting the negative pressure from the pump. In the suction pad portion 2b is disposed a liquid level sensor 2d which detects the liquid level of the blood plasma in the cup 1e and prevents the blood plasma from overflowing the cup 1e. A timing belt 5 (FIG. 1) is passed around the shaft member 4 and a drive pulley 6a of a drive motor 6 and the shaft member 4 is rotated back and forth in response to regular rotation and reverse rotation of the drive motor 6.

Further as shown in FIG. 3, the shaft member 4 is mounted for rotation on a support member 63 fixed to the base 31. A lead screw 64 is supported for rotation between the support member 63 and the base 31. A pulley 65 is fixed to the lower end portion of the lead screw 64. A timing belt 68 is passed around the pulley 65 and a drive pulley 67 of a drive motor 66. A fixed member 69 is fixed to the shaft member 4 and the lead screw 64 extends through a threaded through hole 69a in the fixed member 69 in mesh with the inner thread of the fixed member 69 so that the shaft member 4 is moved up and down in response to rotation of the lead screw 64.

The liquid level sensor 2d is a reflective sensor which projects light such as infrared rays onto the surface of the blood plasma supplied to the cup 1e and optically detects the reflected light from the surface of the blood plasma. The liquid level sensor 2d outputs a maximum signal when the liquid level of the plasma becomes substantially equal to the height of the cup 1e. When the liquid level sensor 2d outputs a maximum signal during filtration of blood, the pressure relief valve is opened to terminate suction of the blood.

Figure 5:
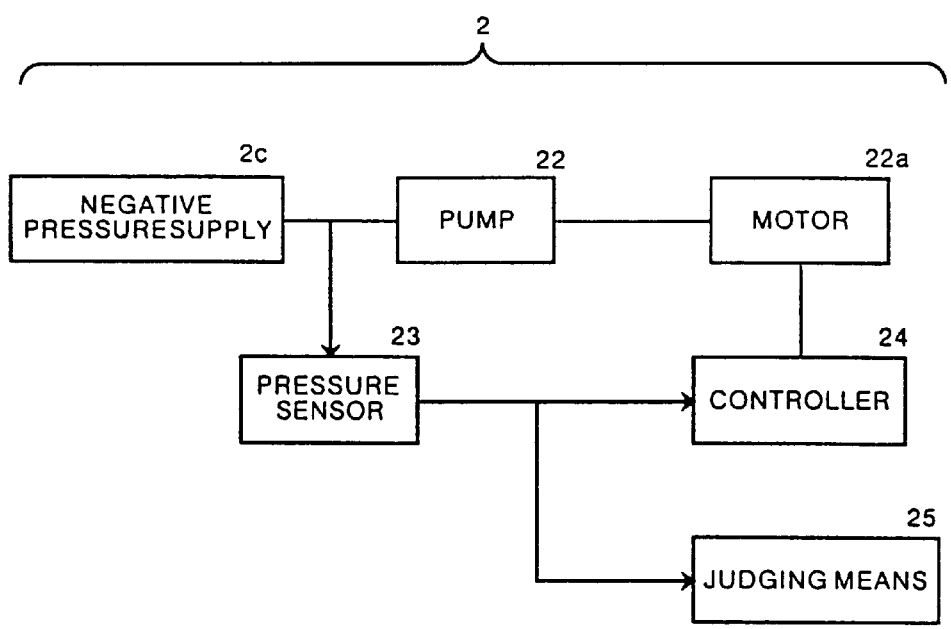
FIG. 5 is a block diagram showing the arrangement of the suction means in the blood filtering unit.

As shown in FIG. 5, the sucking means 2 for applying a negative pressure to the space between the suction pad portion 2b and the lid member 1B of the holder 1 comprises a pump 22 which supplies a negative pressure to the negative pressure supply portion 2c, a motor 22a for driving the pump 22, a pressure sensor 23 which detects the suction pressure supplied to the negative pressure supply portion 2c from the pump 22, a controller 24 which feedback-controls the motor 22a on the basis of the suction pressure detected by the pressure sensor 23, and a judging means 25 which judges that the suction pressure supplied to the negative pressure supply portion 2c from the pump 22 is abnormal on the basis of the output of the pressure sensor 23.

Figure 6:
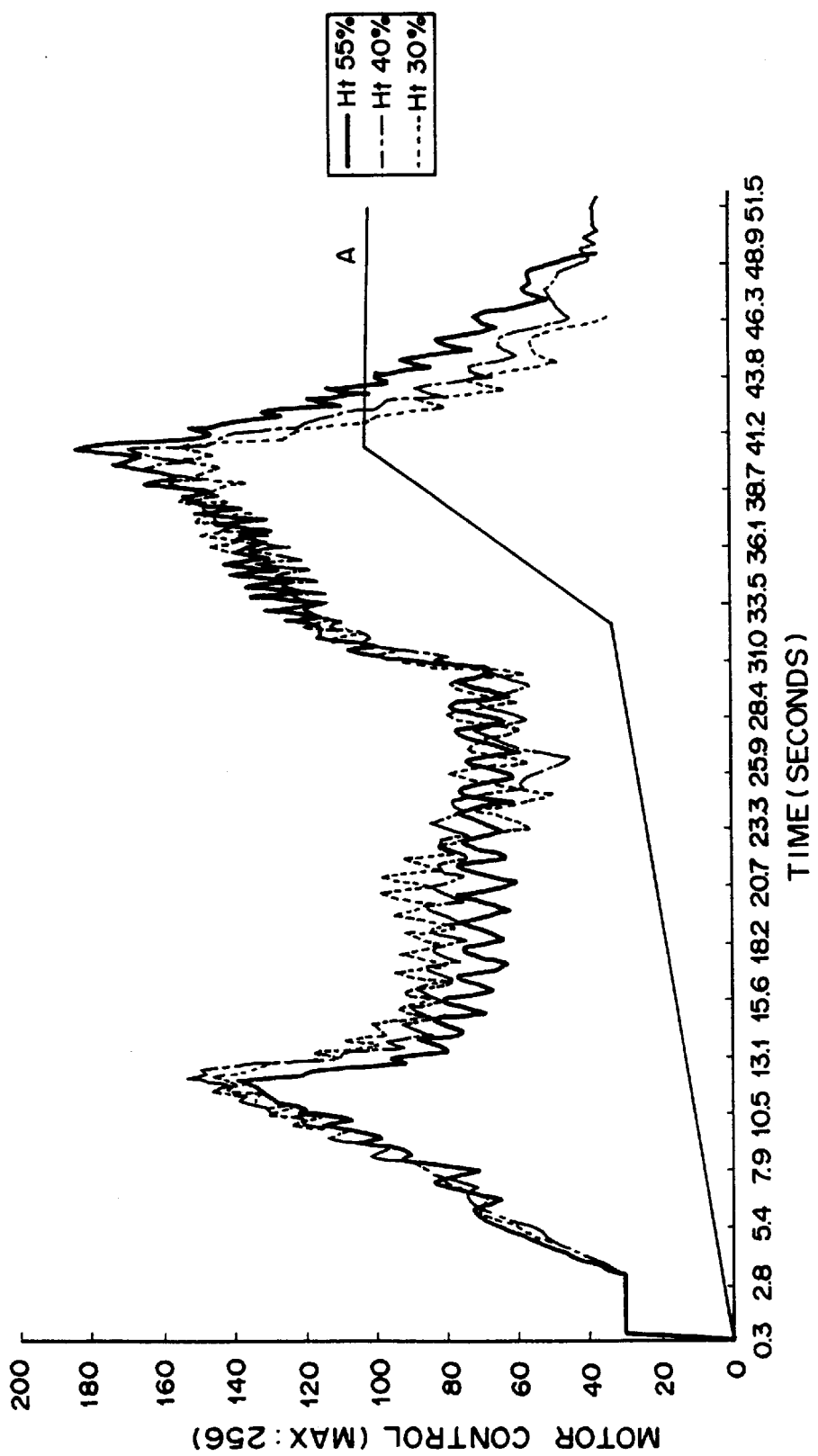
FIG. 6 is a graph showing the pressure control characteristic of the controller of the blood filtering unit.

The controller 24 feedback-controls the motor 22a so that the suction pressure supplied to the negative pressure supply portion 2c changes with time according to a predetermined control characteristic such as shown by the solid line A in FIG. 6. The controlled variable is changed according to the hematcrit of the whole blood.

The judging means 25 judges whether the suction pressure as detected by the pressure sensor 23 conforms to the value determined according to the solid line A and determines that the suction pressure is abnormal when the former deviates from the latter. For example, when the lid member 1B and the suction pad portion 2b are not in abutment against the each other in an air-tight fashion, the suction pressure leaks and cannot be increased higher than a certain value. Further when there is no whole blood to be filtered, the suction pressure is hardly increased with increase in the rotating speed of the motor 22a. When the judging means 25 detects abnormality in the suction pressure, the alarm is given and/or the motor 22a is stopped.

Figure 4:
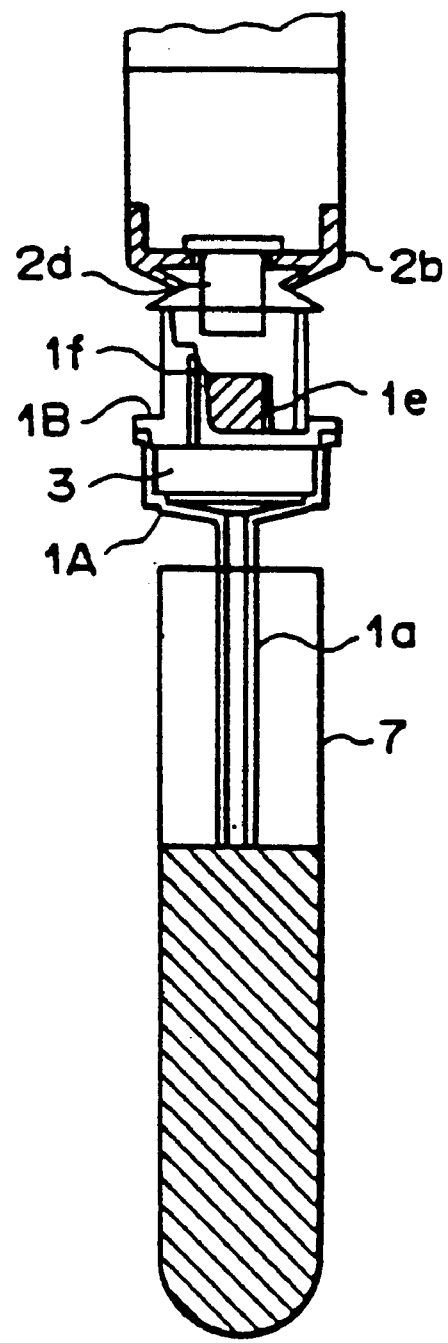
FIG. 4 is a fragmentary front view of the blood filtering unit in operation.

When blood plasma is to be separated from whole blood, the holder 1 is mounted on the blood-gathering tube 7 in the sample holding portion 16 as shown in FIG. 4, and the arm 2a is rotated from an initial position shown by the solid line in FIG. 1 to an operative position shown by the chained line in FIG. 1 so that the suction pad portion 2b of the arm 2a is opposed to the holder 1. Then the arm 2a is moved downward to bring the suction pad portion 2b of the arm 2a into abutment against the lid member 1B of the holder 1. Thereafter the suction pump 22 is operated to supply a negative pressure to the space between the suction pad portion 2b and the lid member 1B, whereby whole blood in the blood-gathering tube 7 is sucked through the plug portion 1a and filtered by the filter 3. Thus blood plasma passing through the filter 3 is supplied to the cup 1e through the supply nozzle 1f.

At this time, the pressure sensor 23 detects the suction pressure of the pump 22. The pressure as detected by the pressure sensor 23 is input into the controller 24 and the rotating speed of the motor 22a is feedback-controlled so that the suction pressure changes with time according to the characteristic curve A. When there is suction pressure leak or when there is no whole blood, the suction pressure cannot be increased with increase in the rotating speed of the motor 22a and the suction pressure as detected by the pressure sensor 23 largely deviates from the characteristic curve A. The judging means 25 detects abnormality in the suction pressure on the basis of the deviation and informs the operator of the abnormality by giving the alarm, stopping the motor 22a and/or stopping suction of the blood by releasing the pressure relief valve in the negative pressure supply portion 2c.

When the whole blood is regularly filtered, blood plasma is supplied to the cup 1e and when the liquid level becomes substantially equal to the height of the cup 1e, the liquid level sensor 2d outputs a maximum signal and the pressure relief valve is opened and the motor 22a is stopped to terminate suction of the blood. Thereafter, the arm 2a is moved upward and returned to the initial position shown by the solid line in FIG. 1. It is possible to inform the operator of end of the filtration by way of a lamp, display on a monitor or sound.

Though, in this embodiment, the suction pressure of the pump 22 is controlled according to characteristic curve A in FIG. 6, it may be controlled in various control characteristics.

Further, though, in this embodiment, abnormality is detected on the basis of deviation of the suction pressure, it may be detected on the basis of deviation of the rotating speed of the motor 22a from those shown in FIG. 6. That is, when there is suction pressure leak or when there is no whole blood to be filtered, the rotating speed of the motor 22a must be greatly increased in order to obtain a suction pressure according to the characteristic curve A. Accordingly, abnormality in the suction pressure can also be detected by monitoring the rotating speed of the motor 22a. Further abnormality in the suction pressure may be detected on the basis of the suction pressure as detected by the pressure sensor 23 and the rotating speed of the motor 22a.

Figure 7:
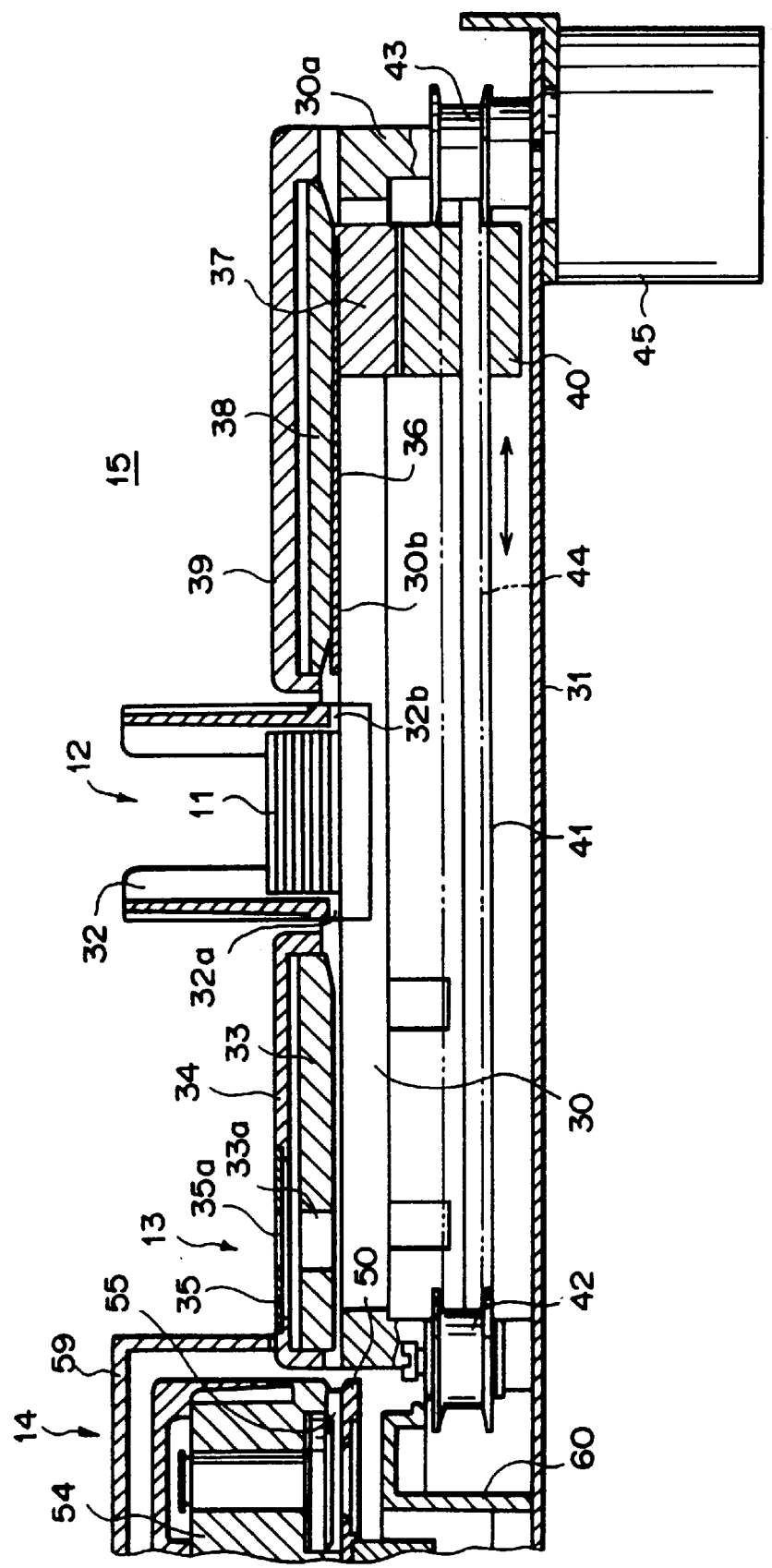
FIG. 7 is a fragmentary cross-sectional view showing the conveyor means.

As shown in FIG. 7, the conveyor means 15 comprises a conveyor table 30 which has legs 30a at the front and rear ends thereof and is placed on the base 31 to extend toward the center of the incubator 14, and the element supply section 12 is located at the middle of the conveyor table 30 and the spotting station 13 is located between the element supply section 12 and the incubator 14.

The element supply section 12 is provided with an element guide 32 which holds the chemical analysis elements 11. Generally a stack of a plurality of virgin chemical analysis elements 11 are held in the element guide 32. The slide guide 32 is mounted on a recess of the conveyor table 30 so that the lowermost one of the chemical analysis elements 11 in the stack is positioned substantially flush with the upper surface of the conveyor table 30. An opening 32a which permits only a single chemical analysis element 11 to pass therethrough is formed in the front face of the element guide 32 at the lowermost portion thereof and an opening which permits insertion of a pusher (to be described later) is formed in the rear face of the element guide 32. Further a slit 32b which communicates with a slit 30b formed in the conveyor table 30 as will be described later is formed in the bottom of the element guide 32. A cartridge in which a stack of a plurality of chemical analysis elements 11 is stored may be set in the slide guide 32.

An element pressing member 33 having a circular opening 33a is disposed at the spotting station 13. The element pressing member 33 is contained for up-and-down movement in a cover 34 fixed above the conveyor table 30. A glass plate 35 provided with a spotting opening 35a is fixed on the top of the cover 34. Further the spotting station 13 is provided with a bar-code reader 130 (FIG. 1) for reading the bar code on the chemical analysis element 11. The bar-code reader 130 is for identifying the terms of examination and the like and for detecting the position (upside down and/or inside out) of the chemical analysis element 11.

The conveyance of the chemical analysis element 11 is effected by forward movement of a plate-like pusher 36 on the conveyor table 30. That is, a slit 30b extends in the longitudinal direction of the conveyor table 30 along the longitudinal axis thereof and the pusher 36 is mounted on the conveyor table 30 to be slidable along the slit 30b. A block 37 which is slidable along the slit 30b on the lower surface of the conveyor table 30 is fixed to the rear end portion of the pusher 36 by way of a connecting member extending through the slit 30b. An auxiliary plate 38 for pressing the pusher 36 against the upper surface of the conveyor table 30 is disposed above the conveyor table 30 behind the element supply section 12. The auxiliary plate 38 is held in a cover 39 to be slightly movable up and down.

A slider 40 is mounted on the bottom of the block 37 and the slider 40 is supported for back and forth movement on a guide rod 41 extending along the conveyor table 30. An endless belt 44 passed around a pair of pulleys 42 and 43 disposed at the front and rear ends of the conveyor table 30 is fixed to the slider 40. The rear pulley 43 is driven by a conveyor motor 45 to slide the pusher 36 by way of the slider 40 and the block 37. The front end of the pusher 36 pushes the rear end face of the chemical analysis element 11 to insert the chemical analysis element 11 linearly into the incubator 14 from the spotting station 13.

The conveyor motor 45 is controlled to convey the lowermost chemical analysis element 11 in the element guide 32 to the spotting station 13, to insert the chemical analysis element 11 spotted with sample liquid into the chemical analysis element receiving portion 55 in the incubator 14 and to convey the chemical analysis element 11 into the discarding hole 56 at the center of the incubator 14 after measurement.

Figure 8:
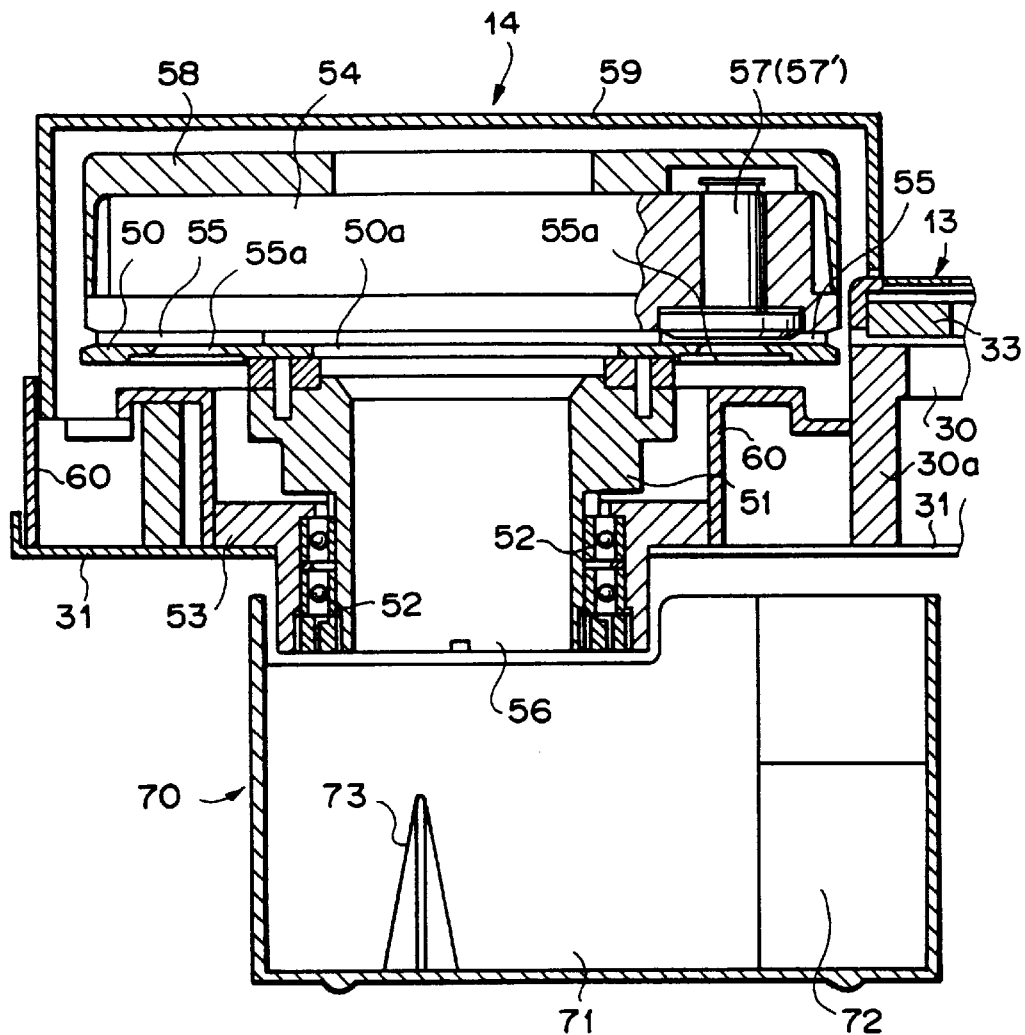
FIG. 8 is a fragmentary cross-sectional showing the incubator.

As shown in FIG. 8, the incubator 14 comprises a disc-like rotary member 50 and an upper member 54 disposed on the rotary member 50. The rotary member 50 is provided with a tubular member 51 at the central portion of the lower surface thereof and the tubular member 51 is supported for rotation on a support member 53 by way of a bearing 52. The lower surface of the upper member 54 is flat and a plurality of (six in this particular embodiment) recesses are formed on the upper surface of the rotary member 50 at regular intervals in a circle, whereby a plurality of thin spaces which form the element receiving portions 55 are formed between the rotary member 50 and the upper member 54. The bottom surface of each element receiving portion 55 is flush with the upper surface of the conveyor table 30 and the outer peripheral surface of the rotary member 50 is positioned near the front end of the conveyor table 30.

The inner hole of the tubular member 51 forms the discarding hole 56. The diameter of the discarding hole 56 is set so that the chemical analysis element 11 can pass through the discarding hole 56. The rotary member 50 is provided with an opening 50a which is formed at the center of the rotary member 50 to communicate with the discarding hole 56. The portion inside the element receiving portion 55 is flush with the bottom surface of the element receiving portion 55 and communicates with the opening 50a so that the chemical analysis element 11 in the element receiving portion 55 can be dropped into the discarding hole 56 by simply pushing the chemical analysis element 11 toward the center of the rotary member 50.

A heating means (not shown) is provided on the upper member 54. By controlling the heating means, the chemical analysis element 11 in the element receiving portion 55 is held at a constant temperature. Further the upper member 54 is provided with a pressing member 57 which presses the mount of the chemical analysis element 11 from above and prevents evaporation of the sample liquid. A cover 58 is provided on the upper surface of the upper member 54. The incubator 14 is covered with upper and lower light-shielding covers 59 and 60. The heating means is controlled to hold the chemical analysis element 11 for measuring the degree of coloring (optical density) at 37±0.2° C. and to hold the chemical analysis element 11 for measuring the ionic activity at 30±0.1° C. That is, the chemical analysis elements 11 must be held at different temperatures according to the purpose of measurement. However, since only a single heating means is provided in this particular embodiment, a pressing member 57' different from the pressing member 57 in shape is used for the chemical analysis element 11' for measuring the ionic activity and at the same the shape of the rotary member 50 is changed at the element receiving portion 55b for receiving the chemical analysis element 11' for measuring the ionic activity as will be described in detail later so that less heat is transmitted to the chemical analysis element 11' for measuring the ionic activity.

An opening 55a for measuring light is formed in the center of the bottom surface of each element receiving portion 55 for receiving the chemical analysis element 11 for measuring the optical density thereof. The light measuring head 27 of the measuring means 18 disposed in the position shown in FIG. 1 measures the amount of light reflected from the chemical analysis element 11 through the opening 55a. One 55b of the element receiving portions 55 is provided with three pairs of probe insertion holes 55c, 55d and 55f (FIG. 1) for measuring ionic activity (to be described later) and the chemical analysis element 11' for measuring the ionic activity is inserted into the element receiving portions 55b.

The incubator 14 is rotated back and forth by a timing belt (not shown) passed around the tubular member 51 of the rotary member 50 and a drive pulley (not shown) of a drive motor. Rotation of the incubator 14 is controlled so that the light measuring head 27 positioned in a predetermined angular position of the incubator 14 is first opposed to a white reference plate and then opposed to a black reference plate. The light measuring head 27 measures the optical densities of the white and black reference plates and calibration is executed. Thereafter the chemical analysis elements 11 in the element receiving portions 55 are brought to the light measuring head 27 in sequence and the optical densities of the chemical analysis elements 11 are measured. Then the incubator 14 is reversed to return to the initial position. When the ionic activity is to be measured, a chemical analysis element 11' is inserted into the element receiving portion 55b and the incubator 14 is rotated to bring the element receiving portion 55b to the analyzer 21. After measurement of the ionic activity, the incubator 14 is reversed to return to the initial position.

A discarding box 70 for gathering chemical analysis elements 11 after measurement is disposed below the incubator 14. The inner space 71 of the discarding box 70 is positioned below the discarding hole 56 in the tubular member 51 of the incubator 14. The discarding box 70 is positioned so that the inner space 71 is shifted in one direction from the center of the incubator 14 due to the layout of other components. An inclined surface 72 is formed in a corner of the inner space 71. The inclined surface 72 is positioned below a tip removing portion 20 (to be described later) and nozzle tips 25 which are changed each time the sample liquid is changed are dropped onto the inclined surface 72. The inclined surface 72 is inclined downward (20 to 45°) toward the inner space 71 so that the nozzle tip 25 dropped onto the surface 72 falls down and are gathered toward the center of the inner space 71.

A projection 73 erects from the bottom of the inner space 71 of the discarding box 70 in a positioned shifted from the center of the discarding hole 56 in the direction opposite to the direction in which the discarding box 70 is shifted from the center of the incubator 14. The tip of the projection 73 is like a ball or needle and the chemical analysis elements 11 dropped into the discarding box 70 through the discarding hole 56 change their directions of travel upon impact against the tip of the projection 73 so that the chemical analysis elements 11 are scattered over the wide area in the discarding box 70.

Figure 9:
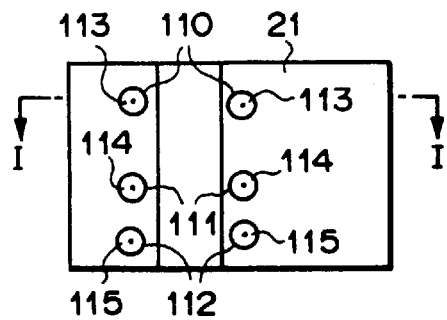
FIG. 9 is a fragmentary plan view showing the analyzer.

As shown in FIG. 1, the analyzer 21 for measuring the ionic activity is positioned below the rotary member 50 of the incubator 14. The basic structure of the analyzer 21 is disclosed, for instance, in U.S. Pat. No. 4,257,862, Japanese Patent Publication Nos. 58(1983)-4981 and 6(1994)-82113 and Japanese Unexamined Patent Publication Nos. 58(1983)-156848 and 58(1983)-211648. As shown in FIGS. 9 and 108, the analyzer 21 is provided with three pairs of through holes 110, 111 and 112 and three pairs of potential measuring probes 113, 114 and 115 are supported for up-and-down movement in the through holes 110, 111 and 112. Since the probes 113, 114 and 114 are the same in arrangement, only the probes 113 will be described, hereinbelow.

Figure 10:
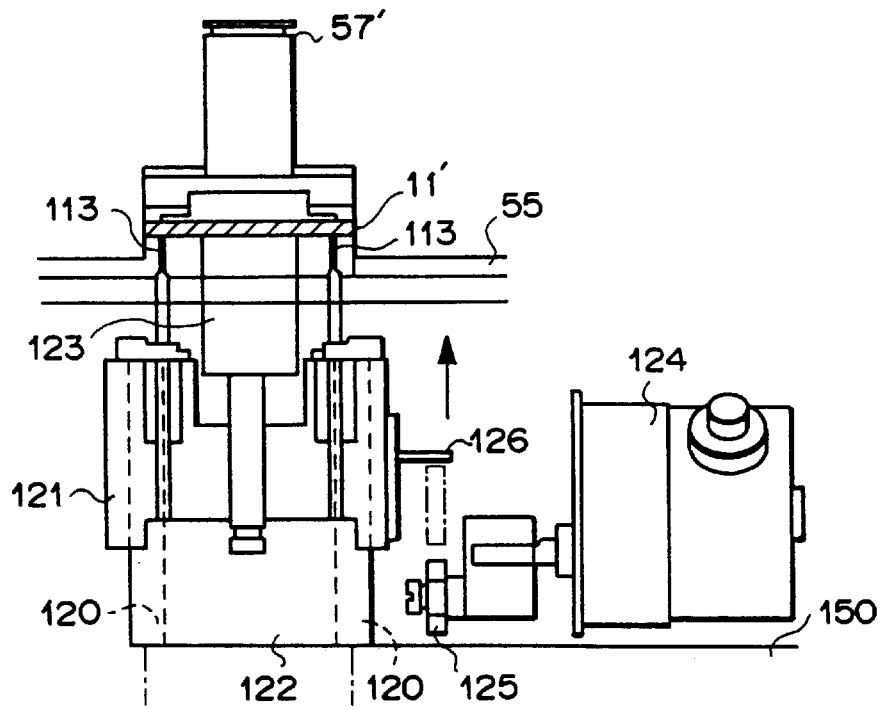
FIG. 10 is a cross-sectional view taken along line I—I in FIG. 9.

As shown in FIG. 10, the probes 113 are fixed to an up-and-down member 121 which is moved up and down along a fixed member 120 erected from a base portion 150 and are in electrical contact with a measuring portion 122 of the analyzer 21. A holding member 123 which holds the chemical analysis element 11' together with the pressing member 57' is mounted on the up-and-down member 121. The pressing member 57' for the chemical analysis element 11' for measuring the ionic activity is concave toward the chemical analysis element 11' in order to reduce the contact area with the element 11' and not to be brought into contact with the sample liquid and/or the reference liquid. The up-and-down member 121 is urged downward in FIG. 10 by a spring not shown. A drive motor 124 is disposed beside the up-and-down member 121 and a cam member 125 is mounted on the output shaft of the drive motor 125 to be opposed to an abutment portion 126 on one side of the up-and-down member 121. In response to rotation of the drive motor 124, the cam member 125 moves from the position shown by the solid line in FIG. 10 to the position shown by the chained line to push upward the up-and-down member 121 by way of the abutment portion 126, whereby the probes 113 and the holding member 123 are moved upward. When the cam member 125 is away from the abutment portion 126, the tips of the probes 113, 114 and 115 are retracted in the analyzer 21. However when the up-and-down member 121 is moved upward, the probes 113, 114 and 115 are projected from the surface of the analyzer 21 and are brought into electrical contact with the ion selective electrodes 11$e$, 11$f$ and 11$g$ of the chemical analysis element 11'.

A chemical analysis element 11' spotted with blood plasma onto the spotting hole 11$c$ and with the reference liquid onto the spotting hole 11$d$ is inserted into the element receiving portion 55$b$ and the rotary member 50 of the incubator 14 is rotated, after incubation for a predetermined time, to bring the receiving portion 55$b$ to the analyzer 21. Then the probes 113, 114 and 115 are moved upward together with the holding member 123. The bottom wall of the element receiving portion 55$b$ is formed with a cutaway portion which is shaped and sized to permit insertion of the holding member 123 and minimizes heat transmission from the rotary member 50 to the chemical analysis element 11' so that the chemical analysis element 11' is held at the temperature described above. The chemical analysis element 11' is held between the pressing member 57' and the holding member 123 and at the same time, the probes 113, 114 and 115 are respectively brought into contact with the ion selective electrodes 11$e$, 11$f$ and 11$g$ of the chemical analysis element 11'. The potential differences between the respective ion selective electrode pairs are measured, whereby the activities of $Cl^-$, $K^+$ and $Na^+$ in the blood plasma are measured. The ionic activities thus measured are displayed on a display such as a liquid crystal panel and/or recorded on a paper.

Figure 11:
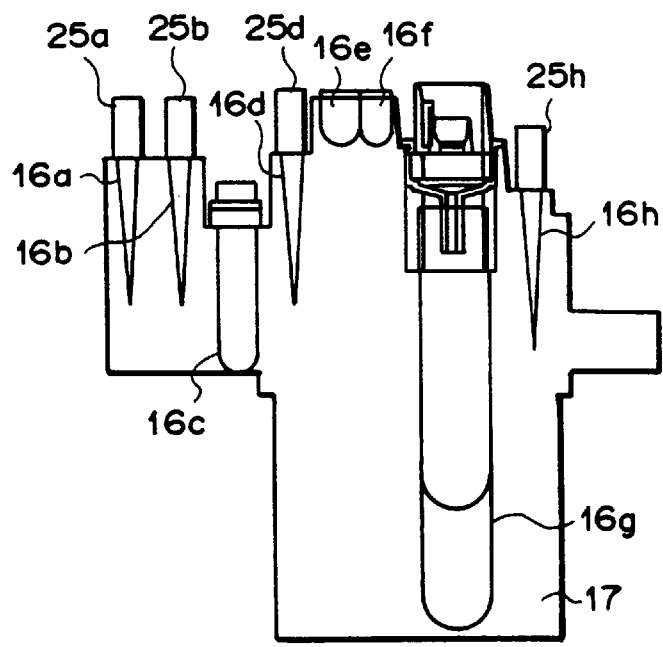
FIG. 11 is a view showing the sample holding portion.

As shown in FIG. 11, the sample holding portion 16 comprises a reference liquid tip holding portion 16$a$ which holds a nozzle tip 25$a$ for the reference liquid, an electrolyte sample tip holding portion 16$b$ which holds a nozzle tip 25$b$ for an electrolyte sample, a reference liquid holding tube 16$c$, a diluent tip holding portion 16$d$ which holds a nozzle tip 25$d$ for diluent, a diluent cup 16$e$, a mixing cup 16$f$, a blood-gathering cup holding portion 16$g$ and a sample liquid tip holding portion 16$h$ which holds a nozzle tip 25$h$ for the sample liquid. The reference liquid tip holding portion 16$a$, the electrolyte sample tip holding portion 16$b$, the reference liquid holding tube 16$c$, the diluent tip holding portion 16$d$, the diluent cup 16$e$, the mixing cup 16$f$, the blood-gathering tube holding portion 16$g$ and the sample liquid tip holding portion 16$h$ are disposed along the path along which spotting nozzles 91$a$ and 91$b$ are moved in response to rotation of a spotting arm 88 of the spotting means 17 as will be described later. The sample holding portion 16 is a consumable good as a whole in this particular embodiment, and is replaceable.

Figure 12:
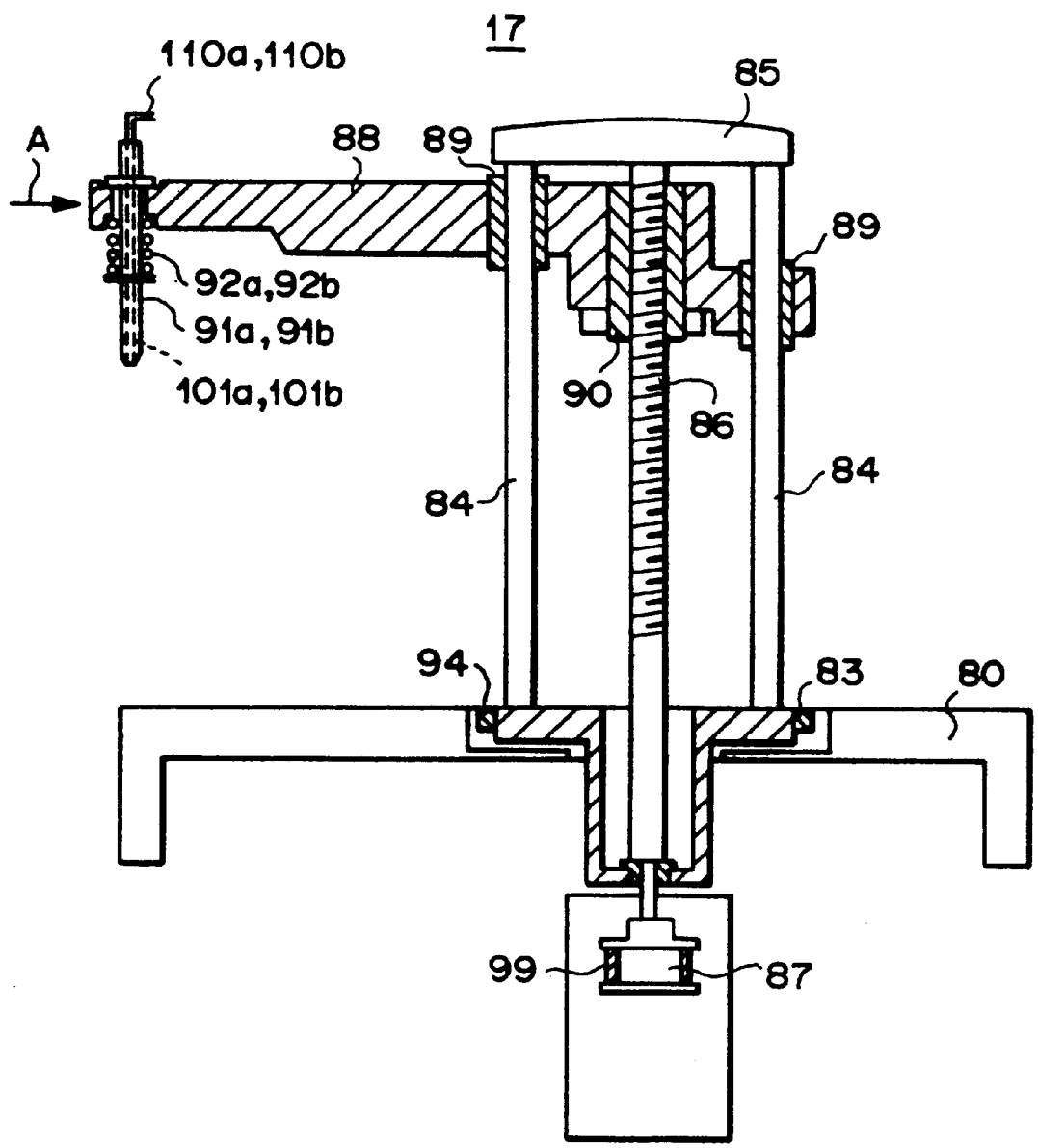
FIG. 12 is a cross-sectional view of the spotting means.

As shown in FIG. 12, a flange member 83 is mounted for rotation by way of a bearing (not shown) on a support member 80 installed on the base 31. A pair of guide rods 84 are erected upward in parallel to each other from the upper surface of the flange member 83. The upper ends of the guide rods 84 are connected to a connecting member 85. A lead screw 86 extends between the connecting member 85 and the flange member 83 and is supported for rotation on the connecting member 85 and the flange member 83. The lower end portion of the lead screw 86 projects downward through the flange member 83 and a pulley 87 is fixed to the lower end of the lead screw 86. A spotting arm 88 is supported on the guide rods 84 to be movable up and down along the guide rods 84 by way of a pair sleeves 89 which are fixed to the base end portion of the spotting arm 88 and slidably fitted on the guide rods 84. A through hole is formed in the base end portion of the spotting arm 88 and a nut member 90 is fixedly fitted in the through hole. The lead screw 86 extends through the base end portion of the spotting arm 88 and is in mesh with the nut member 90, whereby the spotting arm 88 is moved up and down in response to rotation of the lead screw 86.

As clearly shown in FIG. 13, a pair of spotting nozzles 91$a$ and 91$b$ are mounted for up-and-down movement on the free end of the spotting arm 88 and urged downward respectively by a pair of springs 92$a$ and 92$b$. The nozzle 91$a$ is for a sample liquid and an electrolyte sample and the nozzle 91$b$ is for a diluent and a reference liquid. Pipette-like nozzle tips 25$a$, 25$b$, 25$d$ and 25$h$ (will be represented by 25, hereinbelow) are removably mounted on the nozzles 91$a$ and 91$b$. Virgin nozzle tips 25 are set in the sample holding portion 16 and are fitted on the spotting nozzles 91$a$ and 91$b$ in response to downward movement of the spotting arm 88. After use, the nozzle tips 25 are removed from the nozzles 91$a$ and 91$b$ by moving upward the spotting arm 88 with the upper end face of each tip 25 engaged with an engagement groove 20a of a tip removing portion 20 (FIG. 1) and are dropped into the discarding box 70 through an opening 20b.

A timing belt 94 is passed around the flange member 83 and a drive pulley (not shown) on the output shaft of an arm rotating motor (not shown), and the arm rotating motor is rotated in regular and reverse directions to bring the nozzles 91a and 91b to predetermined positions. Further a timing belt 99 is passed around the pulley 87 on the lower end of the lead screw 86 and a drive pulley (not shown) on the output shaft of an arm lifting motor (not shown) and arm lifting motor is rotated in regular and reverse directions to rotate the lead screw 86, thereby moving up and down the spotting arm 88.

Air passages 101a and 101b extend through the spotting nozzles 91a and 91b and air pipes 110a and 110b are connected respectively to the upper ends of the air passages 101a and 101b at their one ends. The other ends of the air pipes 110a and 110b are connected to a syringe 102 (FIG. 1) of a sucking mechanism 19. By operation of the syringe 102, liquid is sucked into the nozzle tips 25 and discharged from the same. A solenoid valve (not shown) is provided in the sucking mechanism 19 and switching between the spotting nozzles 91a and 91b is effected by switching the solenoid valve.

When spotting a liquid onto a chemical analysis element 11, the spotting arm 88 is rotated to bring the nozzle tip 25 above the liquid and is moved downward to dip the nozzle tip 25 in to the liquid. Then the syringe 102 is operated to suck the liquid into the nozzle tip 25. Thereafter the spotting arm 88 is moved upward and is rotated to the spotting station 13 and is moved downward toward the chemical analysis element 11, where the syringe 102 is operated to discharge the liquid held in the nozzle tip 25 onto the chemical analysis element 11.

The operation of the chemical analysis system in accordance with this embodiment will be described with reference to the flow charts shown in FIGS. 15 to 20, hereinbelow.

Before executing analysis, the chemical analysis elements 11 (and/or 11') are set in the chemical analysis element supply section 12 and the sample holding section 16 is set to the system as shown in FIG. 1. At this time, the nozzle tip 25a for the reference liquid, the nozzle tip 25b for an electrolyte sample, the diluent, the nozzle tip 25d for the diluent, the blood-gathering tube 7 and the nozzle tip 25h for the sample liquid are held respectively in the reference liquid tip holding portion 16a, the electrolyte sample tip holding portion 16b, the diluent holding tube 16c, the diluent tip holding portion 16d, the blood-gathering tube holding portion 16g and the sample liquid tip holding portion 16h.

Figure 15:
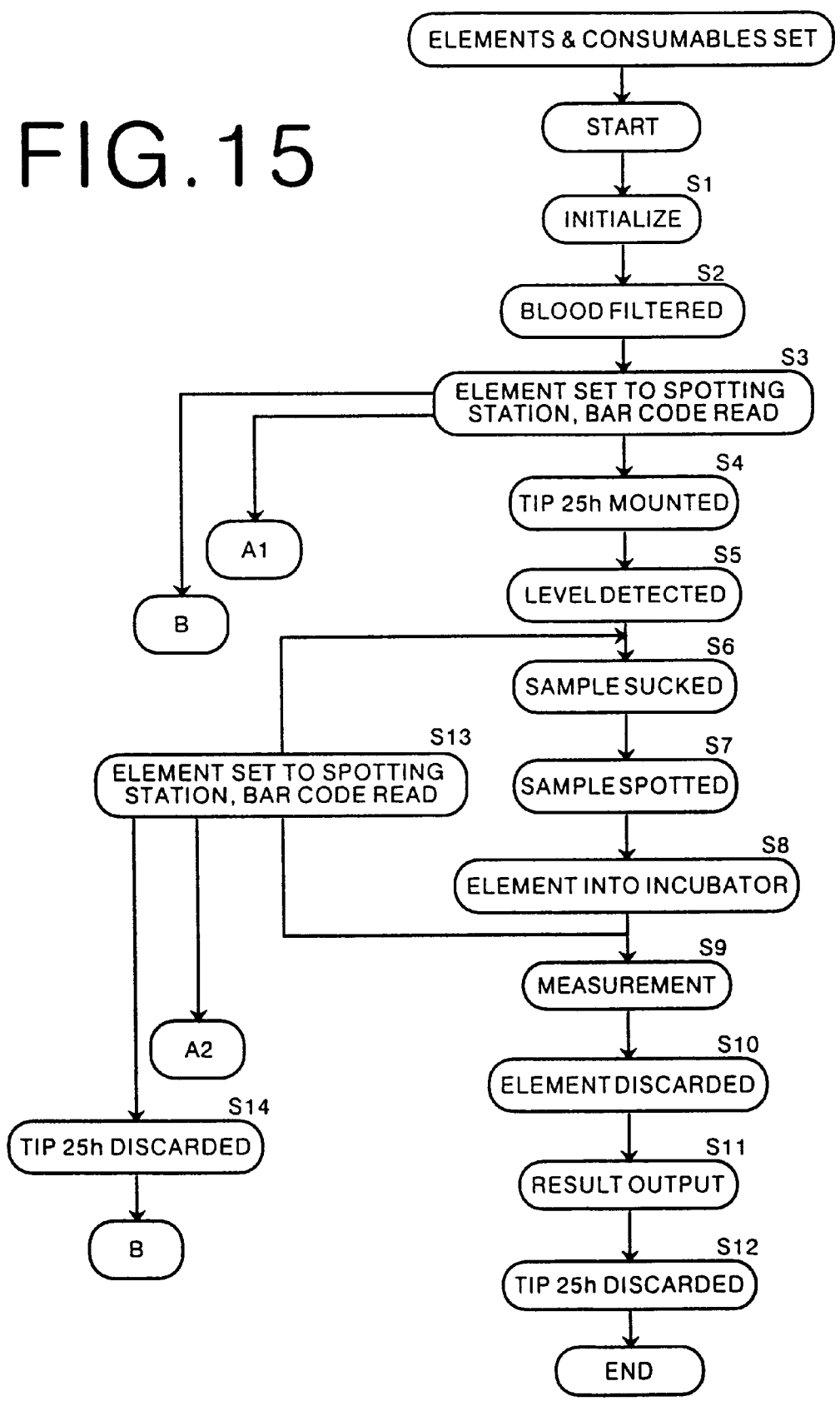
FIG. 15 is a flow chart for illustrating the operation of the chemical analysis system.

In FIG. 15, the chemical analysis system is first initialized. (step S1) Then the whole blood in the blood-gathering tube 7 is filtered to obtain blood plasma. (step S2) The blood filtering procedure executed in step S2 will be described with reference to the flow chart shown in FIG. 16, hereinbelow.

Figure 16:
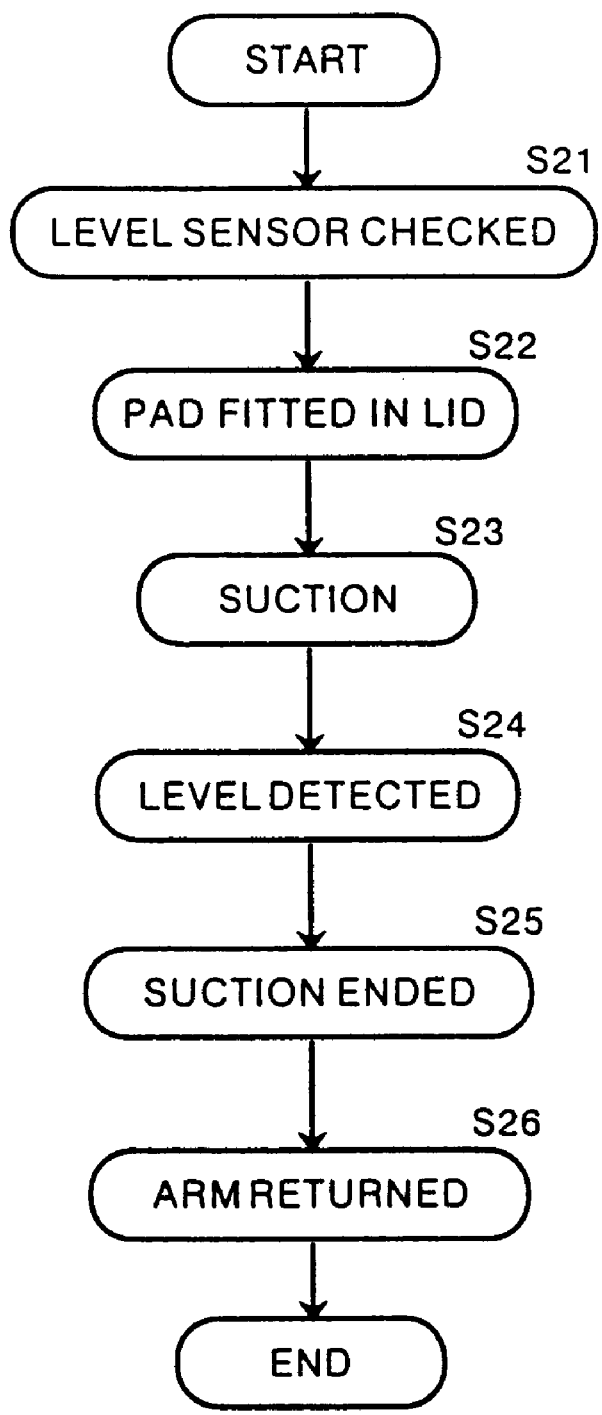
FIG. 16 is a flow chart for illustrating the blood filtering processing.

In FIG. 16, stain of the liquid level sensor 2d is checked and the gain of the liquid level sensor 2d is set by setting a reference plate at the height of the cup 1e. (step S21) Then the arm 2a is rotated to bring the suction pad portion 2b to a position where it is opposed to the holder 1 shown by the chained line in FIG. 1, and the arm 2a is moved downward to bring the suction pad portion 2b into abutment against the lid member 1B of the holder 1. (step S22) Then the pump 22 is operated to apply a negative pressure to the space between the lid member 1B and the suction pad portion 2b, whereby blood plasma passing through the filter 3 is supplied to the cup 1e through the supply nozzle 1f. (step S23) At this time, it is possible to detect leakage and/or the hematocrit of the blood by checking the pressure in the pump 22.

Then when the liquid level sensor 2d detects that a predetermined amount of blood plasma is supplied to the cup 1e, the pump 22 is stopped. (step S24) In place of detecting the liquid level by the liquid level sensor 2d, the pump 22 may be stopped after a predetermined time. Thereafter the pressure relief valve of the negative pressure supply portion 2c is opened to cut supply of the negative pressure from the pump 22 (step S25) and the arm 2a is moved upward to move the suction pad portion 2b away from the lid member 1B and returned to the initial position shown by the solid line in FIG. 1.

Again in FIG. 15, a chemical analysis element 11 is conveyed to the spotting station 13 from the element supply section 12 by the conveyor means 15. Then bar-code reader 130 reads the bar code on the chemical analysis element 11 to detect the terms of examination and the like. (step S3) When the term of examination read is measurement of the ionic activity, the procedure proceeds to B, and when the term of examination read is measurement of the optical density after dilution, the procedure proceeds to A1. When the term of examination read is measurement of the optical density without dilution, the spotting arm 88 is rotated to bring the spotting nozzle 91a to the sample holding portion 16 and the nozzle tip 25h for the sample liquid is mounted on the nozzle 91a. (step S4) Then the liquid level of the sample liquid (blood plasma) in the cup 1e is detected to know the liquid level and to confirm whether a necessary amount of blood plasma exists in the cup 1e. (step S5) The spotting arm 88 is thereafter moved downward and the sample liquid in the cup is sucked into the nozzle tip 25h (step S6), and the spotting arm 88 is driven to bring the nozzle tip 25h to the spotting station 13 and the sample liquid is spotted onto the chemical analysis element 11 through the spotting hole 11a (step S7). At this time, it is possible to detect clogging of the tip 25h by detecting the change in pressure and comparing the change with a reference value.

In step S8, the chemical analysis element 11 spotted with the sample liquid is inserted into the incubator 14 which is held at 37±0.2° C. When a plurality of chemical analysis elements 11 are continuously processed, other chemical analysis elements 11 are conveyed to the spotting station 13 one by one and the bar codes on the elements are read. (step S13) Then steps S6 to S8 are repeated. When the term of examination read is measurement of the ionic activity, the procedure proceeds to B after the nozzle tip 25h is discarded in step S14, and when the term of examination read is measurement of the optical density after dilution, the procedure proceeds to A2.

After the chemical analysis elements 11 are inserted into the incubator 14, the rotary member 50 is rotated to bring the chemical analysis elements 11 in the element receiving portions 55 to the light measuring head 27 in sequence and the reflective optical density of each chemical analysis element 11 is measured by the light measuring head. (step S9) After the measurement, the conveyor means 15 pushes the chemical analysis element 11 toward the center of the incubator 14 and drops the same into the discarding hole 56. (step S10) Thereafter the result of the measurement is output in step S11, and the nozzle tip 25h is removed from the nozzle 91a at the tip removing portion 20 and is discarded in step S12.

Figure 17:
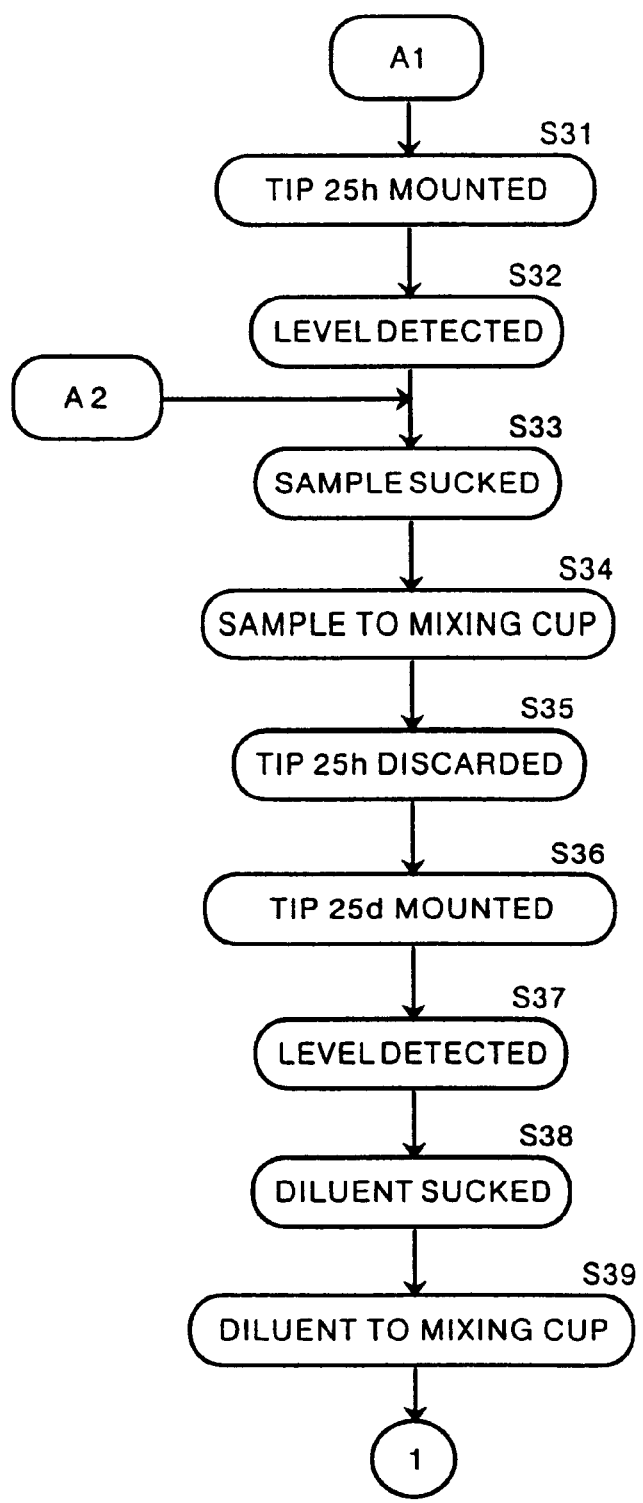
FIGS. 17 and 18 show a flow chart for illustrating the dilution processing.
Figure 18:
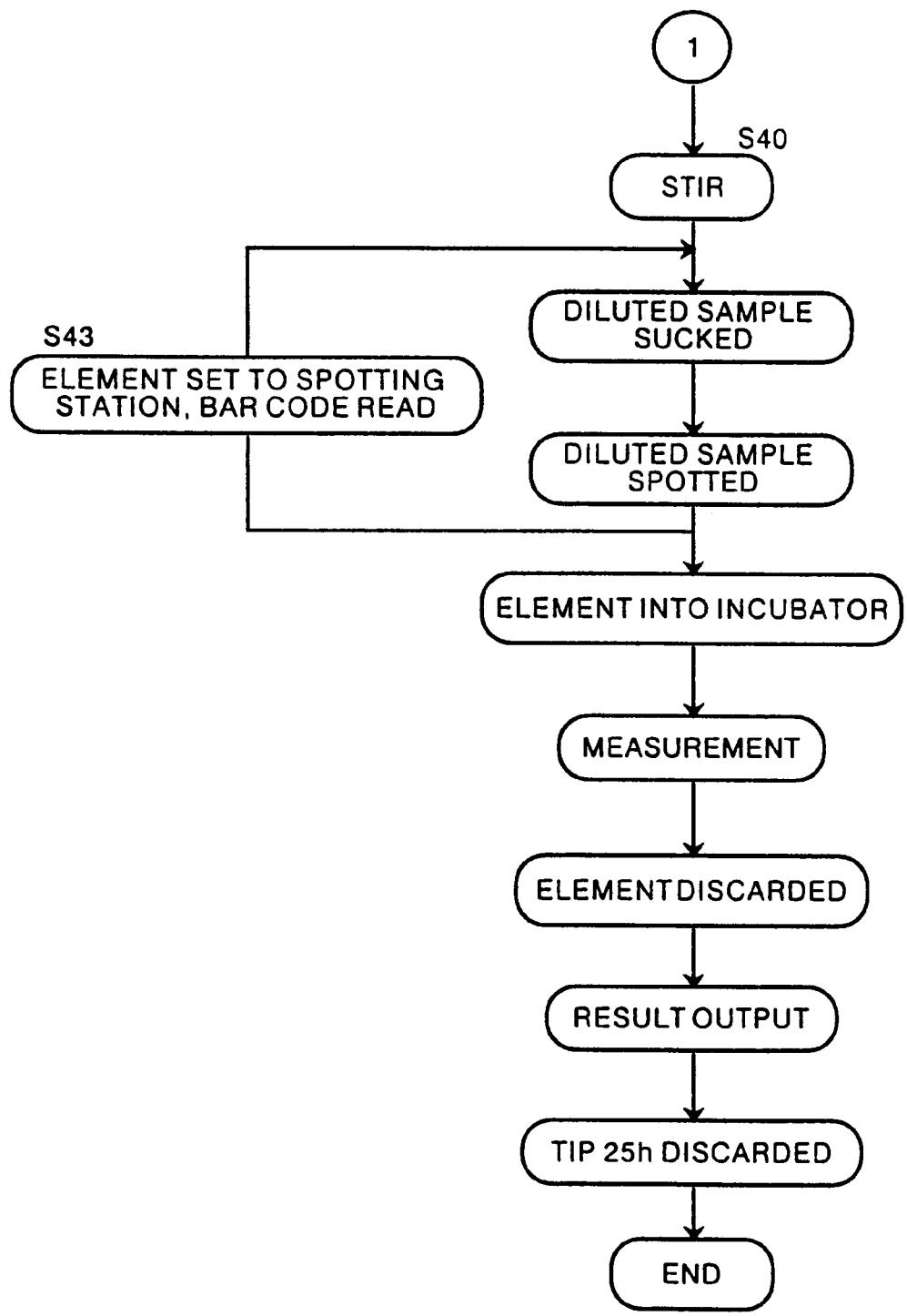

The case where the term of examination is measurement of the optical density after dilution will be described with reference to the flow chart shown in FIGS. 17 and 18, hereinbelow. This examination is executed when the blood is too thick to accurately measure the optical density. In step S31, the spotting arm 88 is rotated to bring the spotting nozzle 91a to the sample holding portion 16 and the nozzle tip 25h for the sample liquid is mounted on the nozzle 91a. Then the liquid level of the sample liquid (blood plasma) in the cup 1e is detected to know the liquid level and to confirm whether a necessary amount of blood plasma exists in the cup 1e. (step S32) The spotting arm 88 is thereafter moved downward and the sample liquid in the cup 1e is sucked into the nozzle tip 25h (step S33). At this time, it is possible to detect clogging of the tip 25h by detecting the change in pressure and comparing the change with a reference value.

Then in step S34, the sample liquid in the nozzle tip 25h is discharged into the mixing cup 16f. The nozzle tip 25h is thereafter removed from the nozzle 91a at the tip removing portion 20 and is discarded in step S35. Thereafter, the spotting arm 88 is rotated to bring the spotting nozzle 91b to the sample holding portion 16 and the nozzle tip 25d for the diluent is mounted on the nozzle 91b. (step S36) Then the liquid level of the diluent in the diluent cup 16e is detected to know the liquid level and to confirm whether a necessary amount of diluent exists in the cup 16e. (step S37) The spotting arm 88 is thereafter moved downward and the diluent in the cup 16e is sucked into the nozzle tip 25d. (step S38) At this time, it is possible to detect clogging of the tip 25d by detecting the change in pressure and comparing the change with a reference value.

Then in step S39, the diluent in the nozzle tip 25d is discharged into the mixing cup 16f. Thereafter, the nozzle tip 25d is dipped into the mixed liquid and sucking and discharging are alternately repeated to stir the mixture. (step S40) After the stir, the diluted sample liquid is sucked into the tip 25d and the spotting arm 88 is driven to bring the nozzle tip 25d to the spotting station 13 and the diluted sample liquid is spotted onto the chemical analysis element 11 through the spotting hole 11a (steps S41 and S42). At this time, it is possible to detect clogging of the tip 25d by detecting the change in pressure and comparing the change with a reference value. When a plurality of chemical analysis elements 11 are continuously processed, other chemical analysis elements 11 are conveyed to the spotting station 13 one by one and the bar codes on the elements are read (step S43) and steps S41 and S42 are repeated.

Then in steps S45 to S49, the chemical analysis element 11 spotted with the diluted sample liquid is inserted into the incubator 14, the rotary member 50 is rotated to bring the chemical analysis elements 11 in the element receiving portions 55 to the light measuring head 27 in sequence, the reflective optical density of each chemical analysis element 11 is measured by the light measuring head, the conveyor means 15 pushes the chemical analysis element 11 toward the center of the incubator 14 and drops the same into the discarding hole 56, the result of the measurement is output, and the nozzle tip 25d is removed from the nozzle 91a and is discarded.

Figure 19:
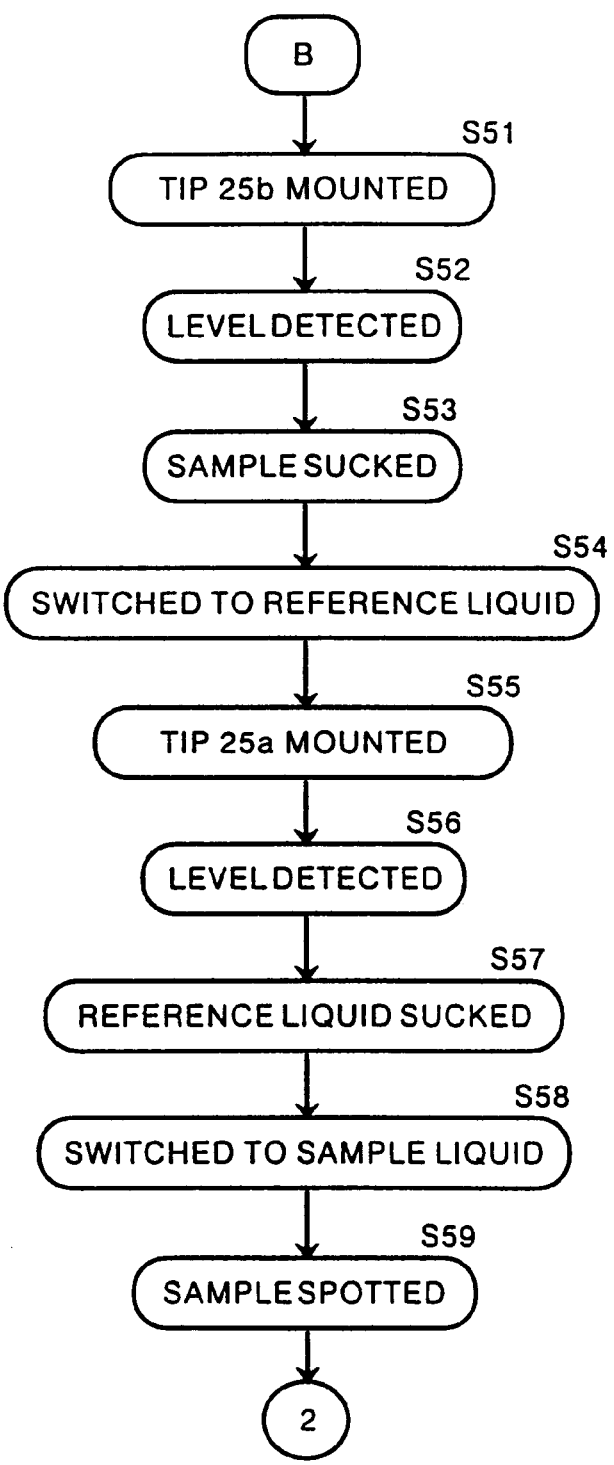
FIGS. 19 and 20 show a flow chart for illustrating the ionic activity measuring processing.
Figure 20:
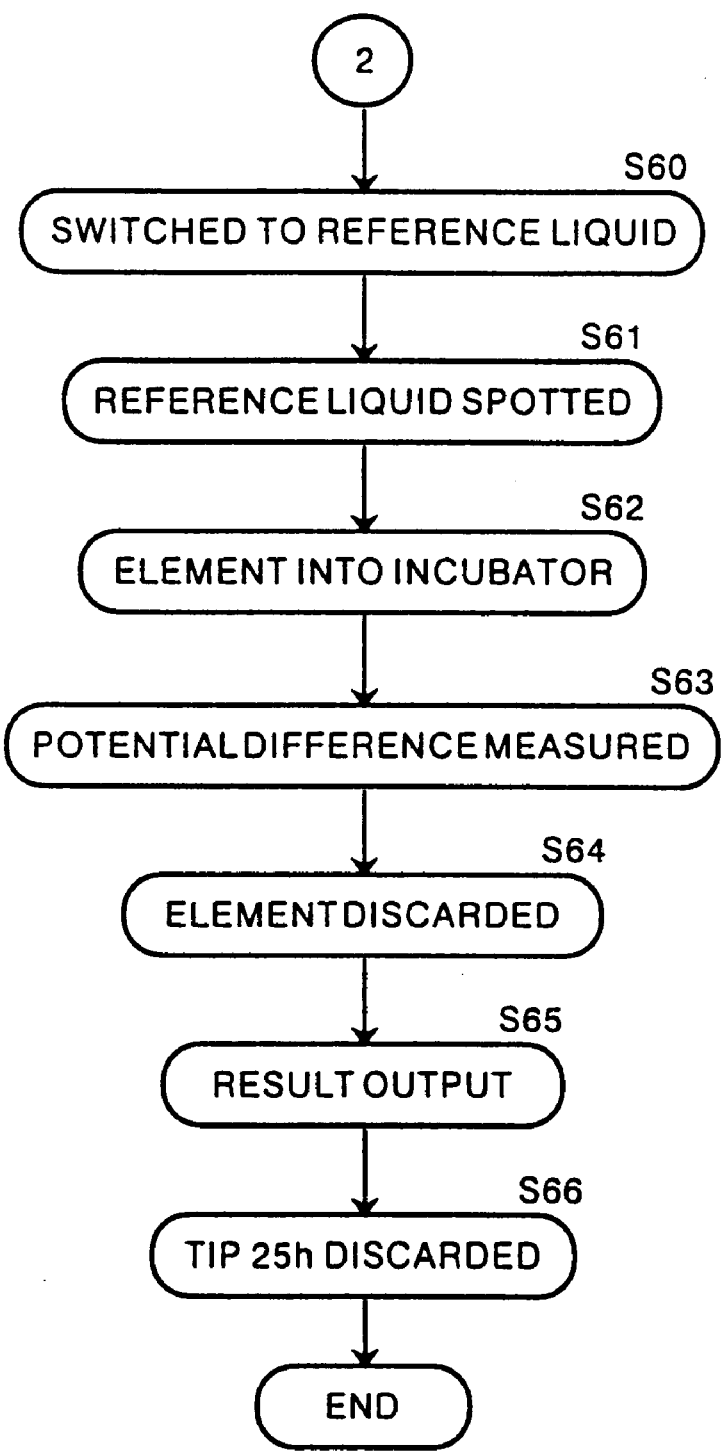

The case where the term of examination is measurement of the ionic activity will be described with reference to the flow chart shown in FIGS. 19 and 20, hereinbelow. In this case, the chemical analysis element conveyed in step S3 in FIG. 15 is a chemical analysis element 11' for measurement of the ionic activity. First the spotting arm 88 is rotated to bring the spotting nozzle 91a to the sample holding portion 16 and the nozzle tip 25b for the electrolyte sample is mounted on the nozzle 91a. (step S51) Then the liquid level of the sample liquid (blood plasma) in the cup 1e is detected to know the liquid level and to confirm whether a necessary amount of blood plasma exists in the cup 1e. (step S52) The spotting arm 88 is thereafter moved downward and the sample liquid in the cup 1e is sucked into the nozzle tip 25b (step S53). At this time, it is possible to detect clogging of the tip 25b by detecting the change in pressure and comparing the change with a reference value.

In step S54, the solenoid valve in the sucking mechanism 19 is switched to switch the flow passage of the pressure to the spotting nozzle 91b. Then the spotting arm 88 is rotated to bring the spotting nozzle 91b to the sample holding portion 16 and the nozzle tip 25a for the reference liquid is mounted on the nozzle 91b. (step S55) Then the liquid level of the reference liquid in the holding tube 16c is detected to know the liquid level and to confirm whether a necessary amount of reference liquid exists in the holding tube 16c. (step S56) The spotting arm 88 is thereafter moved downward and the reference liquid in the holding tube 16c is sucked into the nozzle tip 25a (step S57). At this time, it is possible to detect clogging of the tip 25a by detecting the change in pressure and comparing the change with a reference value.

In step S58, the solenoid valve in the sucking mechanism 19 is switched to switch the flow passage of the pressure to the spotting nozzle 91a. Then the spotting arm 88 is rotated to bring the spotting nozzle 91a to the spotting station 13 and the sample liquid in the nozzle tip 25b is spotted onto the spotting hole 11c of the chemical analysis element 11'. (step S59) Then in step S60, the solenoid valve in the sucking mechanism 19 is switched to switch the flow passage of the pressure to the spotting nozzle 91b and in step S61, the reference liquid in the nozzle top 25a is spotted onto the spotting hole lid of the chemical analysis element 11'.

In step S62, the chemical analysis element 11' spotted with the sample liquid and the reference liquid is inserted into the element receiving portion 55b of the incubator 14 and is held at 30±1° C. After the incubation in the incubator 14, the rotary member 50 is rotated to bring the chemical analysis element 11' in the element receiving portion 55b to the analyzer 21 and the ionic activity is measured by the analyzer 21. (step S63) After the measurement, the conveyor means 15 pushes the chemical analysis element 11' toward the center of the incubator 14 and drops the same into the discarding hole 56. (step S64) Thereafter the result of the measurement is output in step S65, and the nozzle tips 25a and 25b are removed from the nozzles 91a and 91b at the tip removing portion 20 and are discarded in step S66.

As can be seen from the description above, in the chemical analysis system of this embodiment, blood plasma can be separated from whole blood and analyzed by simply loading a blood-gathering tube 7 to the blood filtering unit 9. In the blood filtering unit 9 which separates the plasma from whole blood by filtration under reduced pressure, the plasma can be separated in a shorter time (about one minute) as compared with when the plasma is separated by centrifugal separation (about ten minutes). Accordingly, in the chemical analysis system of this embodiment, it is possible to deal with an emergency.

The number of the element receiving portions 55 in the incubator 14 may be changed as desired and the blood filtering unit 9 may be placed in any position. The chemical analysis system of the present invention may be provided with only one of the measuring means 18 for measuring the optical density and the analyzer 21 for measuring the ionic activity.

What is claimed is:

1. A chemical analysis system for analyzing a sample liquid spotted on a chemical analysis element comprising:

a blood filtering unit comprising a filter which filters whole blood to obtain filtrate, a holder which holds said filter, said holder having a blood inlet and a filtrate outlet, a vacuum which is removably mounted on a side of said holder adjacent to the filtrate outlet and applies a negative pressure to said holder from said side, and a filtrate receiving container disposed adjacent to said filtrate outlet to receive the filtrate, a spotter which spots the filtrate onto a chemical analysis element as the sample liquid, and an analyzer which analyzes the filtrate on said chemical analysis element.

2. A chemical analysis system as defined in claim 1 in which the analyzer comprises both a concentration measurer which is provided to measure concentration of a specific component contained in said sample liquid by measuring optical density of a color formed by a coloring reaction of said sample liquid and a reagent on said chemical analysis element and an ionic activity measurer which is provided to measure ionic activity of a specific ion contained in said sample liquid.

3. A chemical analysis system as defined in claim 1 further comprising a diluter which includes a sample liquid container and dilutes said sample liquid in said container with diluent.

4. A blood filtering unit comprising:

filter which filters whole blood to obtain filtrate, a holder which holds said filter, said holder having a blood inlet and a filtrate outlet, a vacuum which is removably mounted on a side of the holder adjacent to said filtrate outlet and applies a suction pressure to said holder from said side, a pressure sensor which detects the suction pressure of the vacuum, and a controller which controls the vacuum on the basis of the suction pressure detected by the pressure sensor so that the suction pressure is held at a predetermined value.

5. A blood filtering unit as defined in claim 4 further comprising a judger which judges a suction state of the vacuum on the basis of comparison of the suction pressure detected by said pressure sensor and said predetermined value and/or comparison of the speed of a motor for generating the vacuum and a predetermined speed.

6. A blood filtering unit as defined in claim 5 further comprising an error signal generator which generates an error signal when the suction pressure detected by said pressure sensor becomes lower than said predetermined value and/or when the speed of said motor exceeds said predetermined speed.

7. A blood filtering unit as defined in claim 6 further comprising a stopper which stops said vacuum when said error signal is generated.

8. A blood filtering unit as defined in claim 6 further comprising a pressure relief valve which releases the suction pressure to the atmosphere when said error signal is generated.

9. A blood filtering unit as defined in claim 5, wherein said motor has a rotating element and said speed is the rotational speed of said rotating element.

* * * * *